United States Patent

Schoenleber et al.

[11] Patent Number: 5,158,948
[45] Date of Patent: Oct. 27, 1992

[54] TETRACYCLIC SPIROBENZAZEPINE DOPAMINE ANTAGONISTS

[75] Inventors: Robert W. Schoenleber, Deerfield; Paul P. Ehrlich, Evanston; John W. Kebabian, Lake Bluff; James R. Campbell, Ft. Sheridan, all of Ill.

[73] Assignee: Abbott Laboratories, Abbott Park, Ill.

[21] Appl. No.: 762,828

[22] Filed: Sep. 19, 1991

Related U.S. Application Data

[63] Continuation-in-part of Ser. No. 614,908, Nov. 16, 1990, abandoned.

[51] Int. Cl.$^5$ .............. C07D 223/16; C07D 491/107; C07D 495/10; A61K 31/55
[52] U.S. Cl. .................. 514/213; 514/19; 540/543
[58] Field of Search ............ 540/543; 514/19, 213

[56] References Cited

U.S. PATENT DOCUMENTS 5,010,074  4/1991  Gronwald et al. ............ 514/213
5,015,639  5/1991  Berger et al. ............... 514/213

*Primary Examiner*—Mukund J. Shah
*Assistant Examiner*—Philip I. Datlow
*Attorney, Agent, or Firm*—Richard A. Elder; Jerry F. Janssen; Steven F. Weinstock

[57] ABSTRACT

Novel tetracyclic spirobenzazepine compounds of the formula

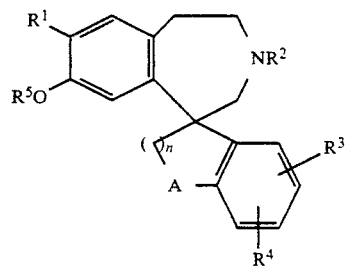

or a pharmaceutically-acceptable salt, amide or ester thereof, which are dopamine D-1 receptor antagonists useful for treating dopamine-related neurological and psychological disorders, cognitive impairment, attention deficit disorders and addictive behavior disorders.

12 Claims, No Drawings

TETRACYCLIC SPIROBENZAZEPINE DOPAMINE ANTAGONISTS

CROSS REFERENCE TO OTHER RELATED APPLICATIONS

This Application is a continuation-in-part of U.S. application Ser. No. 614,908, filed Nov. 16, 1990 now abandoned.

TECHNICAL FIELD

This invention relates to tetracyclic spirobenzazepine compounds and pharmaceutical compositions thereof which are dopamine D-1 receptor antagonists, to processes for making these compounds, to synthetic intermediates employed in these processes and to a method of treating dopamine-related neurological, psychological and behavioral disorders with such compounds.

BACKGROUND OF THE INVENTION

Dopamine is an important neurotransmitter both in the central nervous system (CNS), and in the peripheral nervous system, in which it has important roles, inter alia, in controlling the supply of blood to the kidneys and in autonomic ganglion transmission. It has been postulated that dopamine is involved in several diverse neurological and psychological disorders such as Parkinson's disease and psychoses, and published evidence (reviewed by R. A. Wise and P.-P. Rompre in *Annual Review of Psychology*, 1989, Vol. 40: 191-225) suggests that dopamine also plays a fundamental role in the brain's reward system.

CNS receptors which have a high affinity for dopamine may be divided into two general categories, designated as D-1 receptors and D-2 receptors, based on biochemical and pharmacological differences between the two receptor subtypes, as well as on the molecular biology of dopamine receptors in the CNS. For a thorough review of the classification and function of dopamine receptor subtypes, see C. Kaiser and T. Jain, "Dopamine Receptors: Functions, Subtypes and Emerging Concepts" in *Medicinal Research Reviews*. Vol 5, pp 145-229 (1985).

Stimulation of the dopamine D-1 receptor by dopamine or a dopamine D-1 receptor agonist causes an increase in the production of the second messenger, 3',5'-cyclic adenosine monophosphate (cAMP), by the enzyme adenylate cyclase, which is mediated by a stimulatory G protein.

The biochemical events which follow stimulation of the D-2 receptor by dopamine or a D-2 receptor agonist are not as well understood, however. Autoreceptors on dopaminergic neurons which have the pharmacological properties of D-2 receptors appear to control the firing rate of these neurons as well as the release of dopamine from the nerve terminals. It is also known that stimulation of the D-2 receptors in the intermediate lobe of the pituitary gland causes a decrease in cAMP production and that stimulation of the D-2 receptors on the mammotrophs of the anterior pituitary gland suppresses prolactin secretion. Also, D-2 receptors on the cholinergic interneurons in the striatum (one of the components of the basal ganglia) regulate the release of acetylcholine from these cells.

The putative roles of the two dopamine receptor subtypes also differ in the various neurological and psychological disorders in which dopamine is believed to be involved. Dopaminergic agents that show receptor subtype selectivity therefore potentially have the advantage of eliciting a desired therapeutic response without less desirable side-effects.

Psychoses are serious psychiatric disorders characterized by abnormal behavior including, inter alia, delusions, hallucinations, violence, mania and serious long-lasting depression. Schizophrenia, which was first identified as a disease of the CNS by Kraepelin and Bleuler in the early 1900's, is the most common psychosis and involves disturbance of thought processes, hallucinations and loss of touch with reality. Since the early 1950's, when Delay and Daniker discovered chlorpromazine to be an effective drug for the treatment of schizophrenia, the use of antipsychotic agents for schizophrenia and other psychoses has become widespread and millions of patients have been treated with them. Unfortunately, the currently-available antipsychotic agents frequently produce undesirable side-effects, including commonly, sedation and hypotension, and most commonly, the so-called extrapyramidal neurological effects that include bizarre involuntary movements and Parkinson-like effects. Because of these often-severe side-effects and the high incidence of patients unresponsive to currently-available drugs, more potent and selective agents are needed.

The pioneering work of Carlsson and others led to the now widely-held dopamine theory of schizophrenia. According to this hypothesis (which is supported by several lines of evidence), schizophrenia is caused by a functional overactivity of dopamine in the brain. Chronic abuse of stimulants, such as amphetamines, which are known to enhance dopaminergic activity in the brain, can lead to a paranoid psychosis that is almost indistinguishable from classic paranoid schizophrenia.

The mechanism-of-action postulated for drugs with anti-schizophrenic activity is the blockade by these compounds of the dopamine receptors, and consequently, the prevention of excess dopamine receptor stimulation. In the mid 1970's it was observed that virtually all of the currently-used antipsychotic agents could displace radiolabeled haloperidol (a dopamine D-2 receptor antagonist) from striatal dopamine receptors with a good correlation between average effective clinical dose and drug binding affinity (I. Creese, D. R. Burt and S. H. Snyder, *Science*, 1976, 192: 481-483). It has now been reported, based on the results of preliminary testing in animal models, that D-1 dopamine receptor-selective antagonists may show antipsychotic activity without the liability of producing undesirable extrapyramidal effects (R. E. Chipkin et al., *J. Pharmacology and Experimental Therapeutics*, 1988, 247: 1093-1102).

Recent evidence also suggests that, since dopamine D-1 agonists have proconvulsant activity which is mediated via stimulation of the D-1 receptors (G. Al-Tajir, M. S. Starr and B. S. Starr, *European J Pharmacology*, 1990, 182: 245-251), D-1 antagonists would block this proconvulsant activity and would, therefore, be useful in treating certain types of seizure disorders.

It has further been reported that animals trained to self-administer cocaine will increase their consumption of this drug after treatment with either a D-1 or a D-2 receptor antagonist, possibly in order to maintain the elevated dopamine levels responsible for cocaine's euphorigenic and reinforcing properties. Because of this correlation, dopamine antagonists are potentially also useful for the treatment of drug abuse and other addictive behavior disorders.

Although no dopamine D-1 antagonists are currently being marketed for the indications discussed above, the therapeutic potential of this class of compounds is widely recognized, see, for example, a review article by J. L. Waddington in *General Pharmacology,* 1988, 19: 55–60.

1-Substituted 2,3,4,5-tetrahydro-1H-3-benzazepines, especially compounds with a phenyl ring as the 1-substituent, have been described previously as having dopamine D-1 receptor blocking activity. J. Weinstock et al., in *Drugs of the Future,* 1985, 10: 645–697, discuss the profound effect that 1-phenyl substituents have on the dopaminergic activity of certain types of benzazepines. J. G. Berger, W. K. Chang and M. Peters in International Patent Application Number WO 88/07526, published Oct. 6, 1988, disclose certain 1-substituted 2,3,4,5-tetrahydro-1H-3-benzazepines, including one 1-spirocyclopentane benzazepine derivative, as useful in the treatment of psychoses, depression and pain.

SUMMARY OF THE INVENTION

The present invention is directed to dopamine D-1 receptor antagonists of the formula:

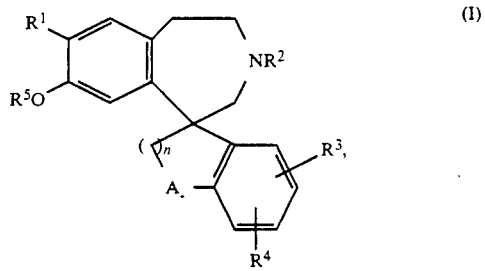

(I)

or pharmaceutically-acceptable salts thereof, wherein n, A, $R^1$, $R^2$, $R^3$, $R^4$ and, $R^5$ are defined below.

The present invention is also directed to pharmaceutical compositions comprising a therapeutically-effective amount of a compound of formula (I) and a pharmaceutically-acceptable carrier or diluent, as well as to a method of treating dopamine-related neurological and psychological disorders, cognitive impairment, attention deficit disorder and addictive behavior disorders in humans and other mammals with a compound of formula (I).

DETAILED DESCRIPTION OF THE INVENTION

This invention relates to novel spirobenzazepine compounds which have the ability to block the action of dopamine at dopamine D-1 receptors in the central and peripheral nervous systems and, therefore, may be used in the treatment of dopamine-related neurological and psychological disorders, as well as in the treatment of cognitive impairment, attention deficit disorders and addictive behavior disorders.

In particular, the invention relates to compounds of formula (I):

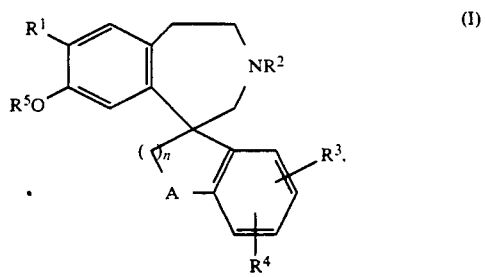

(I)

or pharmaceutically-acceptable salts thereof, wherein
n is an integer of from 1-to-3;
A is $CH_2$, O or S;
$R^1$ is selected from the group consisting of hydrogen, $C_1$–$C_6$-alkyl, halogen, halo-$C_1$–$C_6$-alkyl, as defined below, hydroxy, hydroxy-$C_1$–$C_4$-alkyl, as defined below, $C_1$–$C_6$-alkoxy, as defined below, $C_1$–$C_4$-alkoxymethyl, $C_1$–$C_6$-alkylthio, as defined below, $C_1$–$C_6$-alkoxycarbonyl, $C_1$–$C_6$-alkylcarbonyl, as defined below, aminocarbonyl, as defined below, nitro, amino, aminomethyl, as defined below, $C_1$–$C_6$-alkylamino, as defined below, $C_1$–$C_6$-alkylaminocarbonyl, and alkanoylamino, as defined below;
$R^2$ is selected from hydrogen, $C_1$–$C_6$-alkyl, alkanoyl, α-amino acid and dipeptide, as defined below;
$R^3$ and $R^4$ are independently selected from the group consisting of hydrogen, $C_1$–$C_4$-alkyl, halogen, halo-$C_1$–$C_4$-alkyl, hydroxy, $C_1$–$C_4$-alkoxy, $C_1$–$C_4$-alkylthio, nitro, amino and $C_1$–$C_4$-alkylamino; and
$R^5$ is hydrogen, alkanoyl or aminocarbonyl.

In one embodiment of the present invention, represented by formula (Ia), are compounds wherein A is S and n, $R^1$, $R^2$, $R^3$, $R^4$ and $R^5$ are as defined above:

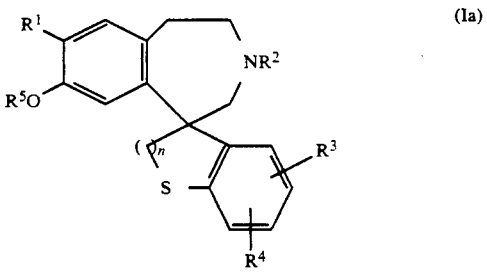

(Ia)

In a preferred embodiment of the present invention, represented by formula (Ib), are compounds wherein A is O and n, $R^1$, $R^2$, $R^3$, $R^4$ and $R^5$ are as defined above:

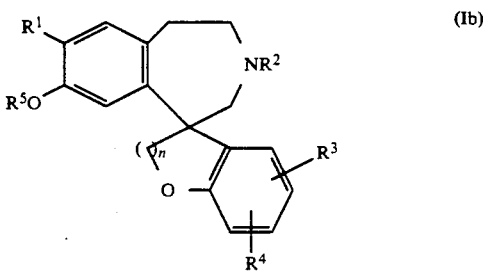

(Ib)

In a most preferred embodiment of the present invention, represented by formula (Ic), are compounds wherein A is CH$_2$ and n, R$^1$, R$^2$, R$^3$, R$^4$ and R$^5$ are as defined above:

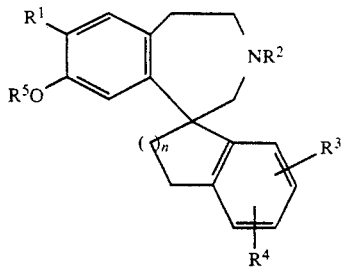

The following are representative of compounds of the present invention:

8-Hydroxy-7-methoxy-1-(spiro-1'-1',2',3',4'-tetrahydronaphthalene)-2,3,4,5-tetrahydro-1H-3-benzazepine;
8-hydroxy-7-methoxy-3-methyl-1-(spiro-1'-1',2',3',4'-tetrahydronaphthalene)-2,3,4,5-tetrahydro-1H-3-benzazepine;
8-Hydroxy-3-methyl-7-methylthio-1(spiro-1'-indan)-2,3,4,5-tetrahydro-1H-3-benzazepine;
8Hydroxy-3-methyl-1-(spiro-1'-indan)-2,3,4,5-tetrahydro-1H-3-benzazepine;
7,8-Dihydroxy-3-methyl-1-(spiro-1'-indan)-2,3,4,5-tetrahydro-1H-3-benzazepine;
7-Bromo-8-hydroxy-1-(spiro-1'-indan)-2,3,4,5-tetrahydro-1H-3-benzazepine;
7-Bromo-8-hydroxy-3-methyl-1-(spiro-1'-indan)-2,3,4,5-tetrahydro-1H-3-benzaepine;
8-Hydroxy-7-nitro-1-(spiro-1'-indan)-2,3,4,5-tetrahydro-1H-3-benzazepine;
7-Amino-8-hydroxy-1-(spiro-1'-indan)-2,3,4,5-tetrahydro-1H-3-benzazepine;
8-Hydroxy-3-methyl-7-nitro-1-(spiro-1'-indan)-2,3,4,5-tetrahydro-1H-3-benzazepine;
7-Amino-8-hydroxy-3-methyl-1-(spiro-1'-indan)-2,3,4,5-tetrahydro-1H-3-benzazepine;
7-Acetylamino-8-hydroxy-3-methyl-1-(spiro-1'-indan)-2,3,4,5-tetrahydro-1H-3-benzazepine;
8-Hydroxy-7-methoxy-1(spiro-1'-indan)-2,3,4,5-tetrahydro-1H-3-benzazepine;
8-Hydroxy-7-methoxy-3-methyl-1(spiro-1'-indan)-2,3,4,5-tetrahydro-1H-3-benzazepine;
7Carboxy-8-hydroxy-1-(spiro-1'-indan)-2,3,4,5-tetrahydro-1H-3-benzazepine;
7,8-Dihydroxy-3-methyl-1-(spiro-1'-1',2',3',4'-tetrahydronapthalene)-2,3,4,5-tetrahydro-1H-3-benzazepine;
8-Hydroxy-3-methyl-1-(spiro-1'-1',2',3',4'-tetrahydronapthalene)-2,3,4,5-tetrahydro-1H-3-benzazepine;
7-Bromo-8-hydroxy-1-(spiro-1'-1',2',3',4'-tetrahydronapthalene)-2,3,4,5-tetrahydro-1H-3-benzazepine;
7-Bromo-8-hydroxy-3-methyl-1-(spiro-1'-1',2',3',4'-tetrahydronapthalene)-2,3,4,5-tetrahydro-1H-3-benzazepine;
8-Hydroxy-7-nitro-1-(spiro-1'-1',2',3',4'-tetrahydronapthalene)-2,3,4,5-tetrahydro-1H-3-benzazepine;
8-Hydroxy-3-methyl-7-nitro-1-(spiro-1'-1',2',3',4'-tetrahydronapthalene)-2,3,4,5-tetrahydro-1H-3-benzazepine;
7-Amino-8-hydroxy-3-methyl-1-(spiro-1'-1',2',3',4'-tetrahydronaphthalene)-2,3,4,5-tetrahydro-1H-3-benzazepines;
7-Acetylamino-8-hydroxy-3-methyl-1-(spiro-1'-1',2',3',4'-tetrahydronaphthalene)-2,3,4,5-tetrahydro-1H-3-benzazepines;
8-Hydroxy-7-methylthio-1-(spiro-1'-1',2',3',4'-tetrahydronapthalene)-2,3,4,5-tetrahydro-1H-3-benzazepine;
8-Hydroxy-3-methyl-7-methylthio-1-(spiro-1'-1',2',3',4'-tetrahydronapthalene)-2,3,4,5-tetrahydro-1H-3-benzazepine;
8-Hydroxy-7-methoxy-3-methyl-1-(spiro-1'-(5'-methyl-1',2',3',4'-tetrahydronaphthalene))-2,3,4,5-tetrahydro-1H-3-benzazepine;
8-Hydroxy-7-methoxy-3-methyl-1-(spiro-1'-(5'-chloro-1',2',3',4'-tetrahydronaphthalene))-2,3,4,5-tetrahydro-1H-3-benzazepine;
8-Hydroxy-7-methoxy-3-methyl-1-(spiro-1'-(5'-fluoro-1',2',3',4'-tetrahydronaphthalene))-2,3,4,5-tetrahydro-1H-3-benzazepine;
8-Hydroxy-3-methyl-1-(spiro-1'-(5'-methoxy-1',2',3',4'-tetrahydronaphthalene))-2,3,4,5-tetrahydro-1H-3-benzazepine;
8-Hydroxy-7-methoxy-3-methyl-1-(spiro-1'-(5',6'-dimethyl-1',2',3',4'-tetrahydronaphthalene))-2,3,4,5-tetrahydro-1H-3-benzazepine;
8-Hydroxy-3-methyl-1-(spiro-1'-(5',6'-dimethoxy-1',2',3',4'-tetrahydronaphthalene))-2,3,4,5-tetrahydro-1H-3-benzazepine;
8-Hydroxy-3-methyl-1-(spiro-1'-(5'-methylindan))-2,3,4,5-tetrahydro-1H-3-benzazepine;
8-Hydroxy-3-methyl-1-(spiro-1'-(5'-chloroindan))-2,3,4,5-tetrahydro-1H-3-benzazepine;
8-Hydroxy-3-methyl-1-(spiro-1'-(5'-fluoroindan))-2,3,4,5-tetrahydro-1H-3-benzazepine;
8-Hydroxy-3-methyl-1-(spiro-1'-(5'methoxyindan))-2,3,4,5-tetrahydro-1H-3-benzazepine;
8-Hydroxy-3-methyl-1-(spiro-1'-(5',6'-dimethoxyindan))-2,3,4,5-tetrahydro-1H-3-benzazepine;
8-Hydroxy-7-methoxy-1-(spiro-5'-(6',7',8',9'-tetrahydro-5'H-benzocycloheptene))-2,3,4,5-tetrahydro-1H-3-benzazepine;
8-Hydroxy-7-methoxy-3-methyl-1-(spiro-5'-(6',7',8',9'-tetrahydro-5'H-benzocycloheptene))-2,3,4,5-tetrahydro-1H-3-benzazepine;
8-Hydroxy-3-methyl-7-methylthio-1-(spiro-5'-(6',7',8',9'-tetrahydro-5'H-benzocycloheptene))-2,3,4,5-tetrahydro-1H-3-benzazepine;
8-Hydroxy-3-methyl-7-nitro-1-(spiro-5'-(6',7',8',9'-tetrahydro-5'H-benzocycloheptene))-2,3,4,5-tetrahydro-1H-3-benzazepine;
7-Bromo-8-hydroxy-3-methyl-1-(spiro-5'-(6',7',8',9'-tetrahydro-5'H-benzocycloheptene))-2,3,4,5-tetrahydro-1H-3-benzazepine;
7-Amino-8-hydroxy-3-methyl-1-(spiro-5'-(6',7',8',9'-tetrahydro-5'H-benzocycloheptene))-2,3,4,5-tetrahydro-1H-3-benzazepine;
7-Acetylamino-8-hydroxy-3-methyl-1-(spiro-5'-(6',7',8',9'-tetrahydro-5'H-benzocycloheptene))-2,3,4,5-tetrahydro-1H-3-benzazepine;
8-Hydroxy-7-methoxy-3-methyl-1-(spiro-4'-(3',4'-dihydro-2'H-1'-benzopyran))-2,3,4,5-tetrahydro-1H-3-benzazepine;
8-Hydroxy-3-methyl-1-(spiro-4'-(3',4'-dihydro-2'H-1'-benzopyran))-2,3,4,5-tetrahydro-1H-3-benzazepine hydrochloride;
7-Bromo-8-hydroxy-3-methyl-1-(spiro-4'-(3',4'-dihydro-2'-H-1'-benzopyran))-2,3,4,5 -tetrahydro-1H-3-benzazepine hydrochloride;

7-Bromo-8-hydroxy-3-methyl-1-(spiro-4'-(3',4'-dihydro-2'H-1'-benzopyran))-2,3,4,5-tetrahydro-1H-3-benzazepine;

8-Hydroxy-3-methyl-7-methylthio-1-(spiro-4'-(3',4'-dihydro-2'H-1'-benzopyran))-2,3,4,5-tetrahydro-1H-3benzazepine;

7,8-Dihydroxy-3-methyl-1-(spiro-4'-(3',4'-dihydro-2'H-1'-benzopyran))-2,3,4,5-tetrahydro-1H-3-benzazepine;

7-Bromo-8-hydroxy-1-(spiro-4'-(3',4'-dihydro-2'H-1'-benzopyran))-2,3,4,5-tetrahydro-1H-3-benzazepine;

8-Hydroxy-3-methyl-7-nitro-1-(spiro-4'-(3',4'-dihydro-2'H-1'-benzopyran))-2,3,4,5-tetrahydro-1H-3-benzazepine;

7-Amino-8-hydroxy-3-methyl-1-(spiro-4'-(3',4'-dihydro-2'H-1'-benzopyran))-2,3,4,5-tetrahydro-1H-3-benzazepine;

8-Hydroxy-7-methoxymethyl-3-methyl-1-(spiro-4'-(3',4'-dihydro-2'H-1'-benzopyran))-2,3,4,5-tetrahydro-1H-3-benzazepine;

3,7-Dimethyl-8-Hydroxy-1-(spiro-4'(3',4'-dihydro-2'H-1'-benzopyran))-2,3,4,5-tetrahydro-1H-3-benzazepine;

7-Acetylamino-8-hydroxy-3-methyl-1-(spiro-4'-(3',4'-dihydro-2'H-1'-benzopyran))-2,3,4,5-tetrahydro-1H-3-benzazepine; and 7-Carbomethoxy-8-hydroxy-3-methyl-1-(spiro-4'-(3',4'-dihydro-2'H-1'-benzopyran))-2,3,4,5-tetrahydro-1H-3-benzazepine;

as well as pharmaceutically-acceptable salts thereof.

The preferred compounds of the invention are compounds of formula (I) in which $R^2$ is methyl or $R^3$ and $R^4$ are both hydrogen.

The following compounds are representative of the preferred compounds of formula (I):

8-Hydroxy-7-methoxy-1-(spiro-1'-1',2',3',4'-tetrahydronaphthalene)-2,3,4,5-tetrahydro-1H-3-benzazepine;

8-Hydroxy-7-methoxy-3-methyl-1-(spiro-1'-1',2',3',4'-tetrahydro-naphthalene)-2,3,4,5-tetrahydro-1H-3-benzazepine;

8-Hydroxy-3-methyl-7-methylthio-1(spiro-1'-indan)-2,3,4,5-tetrahydro-1H-3-benzazepine;

8-Hydroxy-7-methylthio-1-(spiro-1'-indan)-2,3,4,5-tetrahydro-1H-3-benzazepine;

8-Hydroxy-7-methylthio-1-(spiro-1'-1',2',3',4'-tetrahydronapthalene)-2,3,4,5-tetrahydro-1H-3-benzazepine;

8-Hydroxy-3-methyl-1-(spiro-1'-indan)-2,3,4,5-tetrahydro-1H-3-benzazepine;

7,8-Dihydroxy-3-methyl-1-(spiro-1'-indan)-2,3,4,5-tetrahydro-1H-3-benzazepine;

7-Bromo-8-hydroxy-1-(spiro-1'-indan)-2,3,4,5-tetrahydro-1H-3-benzazepine;

7-Bromo-8-hydroxy-3-methyl-1-(spiro-1'-indan)-2,3,4,5-tetrahydro-1H-3-benzazepine;

8-Hydroxy-3-methyl-7-nitro-1-(spiro-1'-indan)-2,3,4,5-tetrahydro-1H-3-benzazepine;

8-Hydroxy-7-methoxy-1-(spiro-1'-indan)-2,3,4,5-tetrahydro-1H-3-benzazepine;

8-Hydroxy-7-methoxy-3-methyl-1-(spiro-1'-indan)-2,3,4,5-tetrahydro-1H-3-benzazepine;

7,8-Dihydroxy-3-methyl-1-(spiro-1'-1',2',3',4'-tetrahydronaphthalene)-2,3,4,5-tetrahydro-1H-3-benzazepine;

8-Hydroxy-3-methyl-1-(spiro-1'-1',2',3',4'-tetrahydronapthalene)-2,3,4,5-tetrahydro-1H-3-benzazepine;

7-Bromo-8-hydroxy-1-(spiro-1'-1',2',3',4'-tetrahydronapthalene)-2,3,4,5-tetrahydro-1H-3-benzazepine;

7-Bromo-8-hydroxy-3-methyl-1-(spiro-1'-1',2',3',4'-tetrahydronapthalene)-2,3,4,5-tetrahydro-1H-3-benzazepine;

8-Hydroxy-3-methyl-7-nitro-1-(spiro-1'-1',2',3',4'-tetrahydronapthalene)-2,3,4,5-tetrahydro-1H-3-benzazepine;

8-Hydroxy-3-methyl-7-methylthio-1-(spiro-1'-1',2',3',4'-tetrahydronapthalene)-2,3,4,5-tetrahydro-1H-3-benzazepine;

8-Hydroxy-7-methoxy-3-methyl-1-(spiro-5'-(6',7',8',9'-tetrahydro-5'H-benzocycloheptene))-2,3,4,5-tetrahydro-1H-3-benzazepine;

8-Hydroxy-7-methoxy-3-methyl-1-(spiro-4'-(3',4'-dihydro-2'H-1'-benzopyran))-2,3,4,5-tetrahydro-1H-3-benzazepine; and 7-Bromo-8-hydroxy-3-methyl-1-(spiro-4'-(3',4'-dihydro-2'H-1'-benzopyran))-2,3,4,5-tetrahydro-1H-3-benzazepine hydrochloride, as well as pharmaceutically-acceptable salts thereof.

The particularly preferred compounds of the present invention are compounds of formula (I) in which $R^2$ is methyl and $R^3$ and $R^4$ are both hydrogen.

The following compounds are representative of the particularly preferred compounds of formula (I):

8-Hydroxy-7-methoxy-3-methyl-1-(spiro-1'-1',2',3',4'-tetrahydro-naphthalene)-2,3,4,5-tetrahydro-1H-3-benzazepine;

8-Hydroxy-3-methyl-7-methylthio-1-(spiro-1'-1',2',3',4'-tetrahydronapthalene)-2,3,4,5-tetrahydro-1H-3-benzazepine;

7,8-Dihydroxy-3-methyl-1-(spiro-1'-indan)-2,3,4,5-tetrahydro-1H-3-benzazepine;

7-Bromo-8-hydroxy-3-methyl-1-(spiro-1'-indan)-2,3,4,5-tetrahydro-1H-3-benzazepine;

8-Hydroxy-7-methoxy-3-methyl-1-(spiro-1'-indan)-2,3,4,5-tetrahydro-1H-3-benzazepine;

7-Bromo-8-hydroxy-3-methyl-1-(spiro-1 2',3',4'-tetrahydronapthalene)-2,3,4,5-tetrahydro-1H-3-benzazepine; and 7-Bromo-8-hydroxy-3-methyl-1-(spiro-4'-(3',4'-dihydro-2'H-1'-benzopyran))-2,3,4,5-tetrahydro-1H-3-benzazepine hydrochloride, as well as pharmaceutically-acceptable salts, amides and esters thereof.

As used herein, the term "alkanoyl" refers to substituents of the formula:

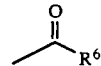

selected from the group of prodrug esters of phenolic compounds and amide prodrugs of amines, which are well known in the art. $R^6$ is selected from $C_1$-$C_6$-alkyl, cyclo-$C_3$-$C_8$-alkyl, adamantyl, phenyl, substituted-phenyl, as defined below, cyclo-$C_3$-$C_8$-alkyl-$C_1$-$C_4$-alkyl, phenyl-$C_1$-$C_4$-alkyl, substituted-phenyl-$C_1$-$C_4$-alkyl, $C_1$-$C_6$-alkoxy, cyclo-$C_3$-$C_8$-alkoxy, as defined below, phenoxy, substituted-phenoxy, as defined below, $C_1$-$C_4$-alkoxy-$C_1$-$C_4$-alkyl, as defined below, cyclo-$C_3$-$C_8$-alkoxy-$C_1$-$C_4$-alkyl, as defined below, phenoxy-$C_1$-$C_4$-alkyl, substituted-phenoxy-$C_1$-$C_4$-alkyl and $C_1$-$C_4$-alkoxycarbonyl-$C_1$-$C_4$-alkyl, as defined below.

"Alkanoylamino" refers to a substituent of the formula $R^7C(O)NH$—, wherein $R^7$ is a $C_1$-$C_6$-alkyl group, a phenyl group or a benzyl group and includes, but is not limited to acetylamino, pivaloylamino and benzoylamino.

"$C_1$-$C_4$-Alkoxy" and "$C_1$-$C_6$-alkoxy", respectively, refer to a branched-or straight-chain alkyl group comprising one-to-four or one-to-six carbon atoms, which is bonded through an oxygen atom. Examples of lower alkoxy groups include methoxy, ethoxy, t-butoxy, and the like.

"$C_1$-$C_4$-Alkoxy-$C_1$-$C_4$alkyl" refers to a $C_1$-$C_4$-alkyl group substituted with a $C_1$-$C_4$-alkoxy group, for example, methoxymethyl, ethoxymethyl, methoxypropyl, isobutyloxymethyl, and the like.

"$C_1$-$C_4$-Alkoxycarbonyl-$C_1$-$C_4$-alkyl" refers to a $C_1$-$C_4$-alkyl group substituted with an $C_1$-$C_4$-alkoxycarbonyl group. Examples of alkoxycarbonylalkyl groups include prodrugs described by Bundgaard et al. in *Int. J. Pharm.*, 1988, 30:111-121 as O-acyloxymethyl derivatives.

"$C_1$-$C_4$-Alkyl" and "$C_1$-$C_6$-alkyl", respectively, refer to branched-or straight-chain alkyl groups comprising one-to-four or one-to-six carbon atoms, including, but not limited to, methyl, ethyl, n-propyl, isopropyl, n-butyl, t-butyl, neopentyl and the like.

"$C_1$-$C_4$-Alkylamino" and "$C_1$-$C_6$-alylamino", respectively, refer to amino groups substituted with either one $C_1$-$C_4$-alkyl group or one $C_1$-$C_6$-alkyl group and hydrogen, or with two $C_1$-$C_4$-alkyl groups or two $C_1$-$C_6$-alkyl groups, including methylamino, ethylamino, dimethylamino, diethylamino, propylamino and ethylmethylamino.

"$C_1$-$C_4$-Alkylthio" and "$C_1$-$C_6$-alkylthio", respectively refer to a $C_1$-$C_4$-alkyl group or a $C_1$-$C_6$-alkyl group which is attached to the aromatic ring through a sulfur atom. Examples of lower alkylthio groups include methylthio, ethylthio, propylthio and the like.

"Amino acid" refers to a single $\alpha$-amino acid, which may either be naturally-occurring amino acids, such as valine, glycine, norvaline, alanine, glutamic acid, glutamine, aspartic acid, leucine, isoleucine, proline, methionine, or phenylalanine, or they may be synthetic amino acids such as cyclohexylalanine or cyclohexylglycine. The amino acids may either be in the L or D configuration or be a mixture of the two isomers. If not otherwise specified, amino acid substituents are optically active and have the L configuration.

"Aminomethyl" as used herein refers to a group of the formula —($CH_2$)—$NR^8R^9$ wherein $R^8$ and $R^9$ are independently selected from hydrogen and $C_1$-$C_4$-alkyl. or $R^8$ and $R^9$ taken together with the nitrogen atom of the amino group form azetidinyl, pyrrolidinyl, piperidinyl, N-alkylpiperazinyl, morpholino, thiomorpholino or hexahydroazepinyl.

"Aminocarbonyl" refers herein to substituents of the formula —C(O)—$NR^{10}R^{11}$ and represents prodrug carbamate esters of the compounds of formula (I). Examples of such carbamate esters are compounds wherein $R^{10}$ and $R^{11}$ are independently selected from hydrogen, $C_1$-$C_6$-alkyl, cycloalkyl, aryl, as defined below, aralkyl, as defined below, hydroxy-$C_1$-$C_6$-alkyl, $C_1$-$C_4$-alkoxy-$C_1$-$C_4$-alkyl, or amino-$C_1$-$C_4$-alkyl, as defined above. Also contemplated are carbamate esters in which one of $R^{10}$ and $R^{11}$ taken together with the nitrogen atom is azetidinyl, pyrrolidinyl, piperidinyl, morpholino, N-alkylpiperazinyl, N-alkoxyalkylpiperazinyl, N-hydroxyalkylpiperazinyl, 3-hydroxyazetidinyl, 3-alkoxyazetidinyl, 3-hydroxypyrrolidinyl, 3-alkoxypyrrolidinyl, 3-or 4-hydroxypiperidinyl, 3- or 4-alkoxypiperidinyl, 4-oxopiperidinyl or 3-oxopiperidinyl. Preferably one of $R^{10}$ and $R^{11}$ is hydrogen.

"Aralkyl" refers to a straight- or branched-chain radical of one-to-six carbon atoms which is substituted with an aryl group, as defined below. Representative aralkyl groups include benzyl, phenethyl groups, fluorobenzyl and fluorophenethyl.

"Aryl" refers to a $C_6$-monocyclic aromatic ring system or a $C_{10}$-bicyclic carbocyclic ring system having one or more aromatic rings including, but not limited to, phenyl, naphthyl, and the like. Aryl groups may be unsubstituted or substituted with one, two or three substituents independently selected from $C_1$-$C_6$-alkyl, as defined above, halo-$C_1$-$C_6$-alkyl, as defined below, $C_1$-$C_6$-alkoxy, as defined above, $C_1$-$C_6$-alkylthio, as defined above, $C_1$-$C_6$-alkoxycarbonyl, hydroxy, halo, as defined below, mercapto, nitro, amino, $C_1$-$C_6$-alkylamino, as defined above, carboxaldehyde, carboxy and carboxamide.

"Cyclo-$C_3$-$C_8$-alkyl" refers to a saturated carbon cyclic group of from three-to-eight carbon atoms, including cyclohexyl, cyclopropyl, cyclooctyl, and the like.

"Cyclo-$C_3$-$C_8$-alkyl-$C_1$-$C_4$-alkyl" refers to a $C_1$-$C_4$-alkyl group substituted with a cyclo-$C_3$-$C_8$-alkyl group, for example cyclohexylmethyl, or cyclopropylmethyl.

"Cyclo-$C_3$-$C_8$-alkyloxy" refers to a cyclo-$C_3$-$C_8$-alkyl group, as defined above, attached through an oxygen atom, for example, cyclopropyloxy, cyclopetyloxy, and the like.

"Cyclo-$C_3$-$C_8$-alkyloxy-$C_1$-alkyloxy-$C_1$-$C_4$-alkyl" refers to a $C_1$-$C_4$-alkyl group substituted with a cyclo-$C_3$-$C_8$-alkoxy group, for example, cyclopropyloxyethyl, cyclohexylmethyl, and the like. "Dipeptide" refers to two $\alpha$-amino acids, defined above, joined by an amide (peptide) bond.

"Halogen" refers to bromo (Br), chloro (Cl), fluoro (F) or iodo (I).

"Halo-$C_1$-$C_4$-alkyl" and "halo-$C_1$-$C_6$-alkyl", respectively, refer to a $C_1$-$C_6$-alkyl group having from one-to-three halogen substituents, for example, chloromethyl, fluoromethyl, chloroethyl, trifluoromethyl, and the like.

"Hydroxy-$C_1$-$C_4$-alkyl" refers to a substituent of formula —C(OH)$R^{12}R^{13}$, wherein $R^{12}$ and $R^{13}$ are independently selected from $C_1$-$C_4$-alkyl and cyclo-$C_3$-$C_8$-alkyl.

"Phenol-protecting group" is used herein to mean substituents on the phenolic oxygen which prevent undesired reactions and degradations during a synthesis. Commonly used phenol-protecting groups include ethers, for example alkyl, alkenyl and cycloalkyl ethers (such as methyl, isopropyl, t-butyl, cyclopropylmethyl, cyclohexyl, allyl ethers and the like); alkoxyalkyl ethers such as methoxymethyl or methoxyethoxymethyl ethers and the like; alkylthioalkyl ethers such as methylthiomethyl ethers; tetrahydropyranyl ethers; arylalkyl ethers (such as benzyl, o-nitrobenzyl, p-methoxybenzyl, 9-anthrylmethyl, 4-picolyl ethers and the like); trialkylsilyl ethers such as trimethylsilyl, triethylsilyl, t-butyldimethylsilyl, t-butyldiphenylsilyl ethers and the like; alkyl and aryl esters such as acetates, propionates, n-butyrates, isobutyrates, trimethylacetates, benzoates and the like; carbonates such as methyl, ethyl, 2,2,2-trichloroethyl, 2-trimethylsilylethyl, vinyl, benzyl and the like; and carbamates such as methyl, isobutyl, phenyl, benzyl, dimethyl and the like.

"Protecting group" or "protected" is well known in the art and refers to substituents on functional groups of compounds undergoing chemical transformation which prevent undesired reactions and degradations during a synthesis; see, for example, T. H. Greene, *Protective Groups in Organic Synthesis*, John Wiley & Sons, New York (1981).

"Prodrug ester group" and "prodrug amide group" are used herein to mean substituents which are rapidly cleaved in vivo, for example by hydrolysis in blood, to yield the parent compounds of the formula (I). The term "prodrug" is well known in the art, see, for example, T. Higuchi and V. Stella in "Pro-drugs as Novel Delivery Systems", Vol 14 of the *A.C.S. Symposium Series*, American Chemical Society (1975) and *Bioreversible Carriers in Drug Design*, E. B. Roche (Ed.), Pergamon Press, New York:1987 for a thorough discussion of the prodrug concept. Examples of esters useful as prodrugs for compounds containing phenol groups include, but are not limited to simple alkyl and aryl esters such as acetates, propionates, n-butyrates, isobutyrates, trimethylacetates, benzoates; carbonates such as methyl, ethyl, 2,2,2-trichloroethyl, 2-trimethylsilylethyl, vinyl, benzyl and carbamates, such as methyl, isobutyl, phenyl and benzyl. Additional examples may be found in the references cited above. The prodrug esters and amides contemplated are defined herein above.

"Substituted-phenoxy" refers to a phenoxy group on which from 1-to-3 of the hydrogen atoms are replaced by a group selected from $C_1$-$C_4$-alkyl, halogen, halo-$C_1$-$C_4$-alkyl, hydroxy, $C_1$-$C_4$-alkoxy, $C_1$-$C_4$-alkylthio, or one hydrogen atom is replaced by a nitro, amino or $C_1$-$C_4$-alkylamino group.

"Substituted-phenyl" refers to a phenyl group on which from 1-to-3 of the hydrogen atoms are replaced by a group selected from $C_1$-$C_4$-alkyl, halogen, halo-$C_1$-$C_4$-alkyl, hydroxy, $C_1$-$C_4$-alkylthio.or one hydrogen atom is replaced by a nitro, amino or $C_1$-$C_4$-alkylamino group and one or two of the remaining hydrogen atoms may be replaced by a group selected from $C_1$-$C_4$-alkyl, halogen, halo-$C_1$-$C_4$-alkyl, hydroxy, $C_1$-$C_4$-alkoxy, and $C_1$-$C_4$-alkylthio.

"Pharmaceutically-acceptable salts" refers to those salts, amides and esters which are, within the scope of sound medical judgement, suitable for use in contact with the tissues of humans and lower animals without undue toxicity, irritation, allergic response and the like, and are commensurate with a reasonable benefit/risk ratio. Pharmaceutically-acceptable salts are well known in the art, see, for example, S. M Berge, et al., *J. Pharmaceutical Sciences*, 1977, 66: 1-19. These salts may be prepared according to conventional methods in situ during the final isolation and purification of the compounds of formula (I), or separately by reacting the free base with a suitable organic acid or base. Representative acid addition salts of the amine include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, hydrobromide, hydrochloride, hydroiodide, 2-hydroxy-ethanesulfonate, lactobionate, lactate, laurate, laurl sulfate, maleate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts of the phenolic hydroxyl group include sodium, calcium, potassium, magnesium salts and the like.

The compounds of formula (I) contain one or more asymmetric carbon atoms and thus exist as pure enantiomers, pure diastereomers, mixtures of enantiomers, mixtures of diastereomers, racemic mixtures of enantiomers, diastereomeric racemates or mixtures of diastereomeric racemates. The present invention anticipates and includes within its scope of all of these isomeric forms. The terms "R" and "S" configuration used herein are as defined by IUPAC 1974 Recommendations for Section E, Fundamental Stereochemistry, Pure Appl. Chem. (1976) 45: 13–30.

The compounds of the present invention may be synthesized as shown in reaction schemes I through X presented below, in which P represents a protecting group and n, A, $R^1$, $R^2$, $R^3$, $R^4$, $R^5$, $R^6$, $R^7$, $R^8$, $R^9$, $R^{10}$ and $R^{11}$ are as defined for formula (I), using the reactions and techniques described in this section. The reactions are performed in a solvent appropriate to the reagents and materials employed and suitable for the transformation being effected. It is understood by those skilled in the art of organic synthesis that the functionality present on the phenyl ring and other portions of the molecule must be consistent with the chemical transformation proposed. This will frequently necessitate judgment as to the order of synthetic steps, protecting groups required and deprotection conditions. Throughout the following section, all compounds of formula (I) falling into a given class may not necessarily be prepared by the methods described for that general class. Substituents on the starting materials may be incompatible with some of the reaction conditions required in some of the methods described. In those cases, alternative methods described elsewhere in the schemes must be utilized; such restrictions to the substituents which are compatible with the reaction conditions will be readily apparent to one skilled in the art.

The condensation of the amino group with an amino acid or dipeptide to give prodrug amide derivatives (compounds of formula (I) wherein $R^2$ is an amino acid or dipeptide) may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in *Peptide Synthesis* Second Edition, M. Bodansky, Y. S. Klausner and M. A. Ondetti (1976).

As in conventional peptide synthesis, branched chain amino and carboxyl groups at the alpha and omega positions in the amino acids may be protected and deprotected if necessary. The protecting groups for amino groups which can be used involve, for example, benzyloxycarbonyl (Z), o-chloro-benzyloxycarbonyl ((2-Cl)Z), p-nitrobenzyloxycarbonyl (Z(NO₂)), p-methoxybenzyloxycarbonyl (Z(OMe)), t-butoxycarbonyl (Boc), t-amyloxycarbonyl (Aoc), isobornealoxycarbonyl, adamantyloxycarbonyl (Adoc), 2-(4-biphenyl)-2-propyloxy carbonyl (Bpoc), 9-fluorenylmethoxycarbonyl (Fmoc), methylsulfonylethoxy carbonyl (Msc), trifluoroacetyl, phthalyl, formyl, 2-nitrophenylsulfenyl (Nps), diphenylphosphinothioyl (Ppt) and dimethylphosphinothioyl (Mpt).

The examples of protecting groups for carboxyl groups involve, for example, benzyl ester (OBn), cyclohexyl ester, 4-nitrobenzyl ester (OBnNO2), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferably that, for example, the guanidino group ($N^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like, and the thiol group in cysteine may be protected with benzyl, p-methoxybenzyl, triphenylmethyl, acetomidomethyl, ethylcarbamyl, 4-methylbenzyl (4-MeBn, 2,4,6,-trimethylbenzyl (Tmb) and the like, and the hydroxy group in serine may be protected with benzyl (Bn), t-butyl, acetyl, tetrahydropyranyl (THP) and the like.

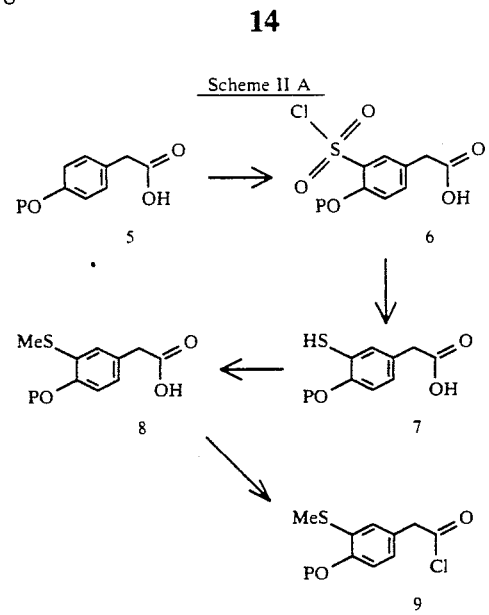

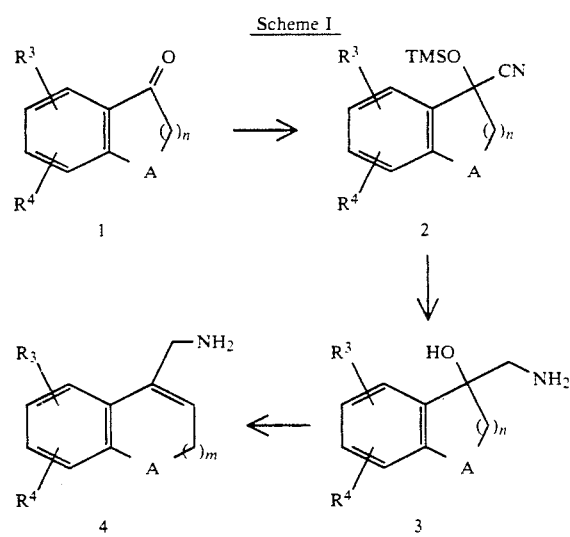

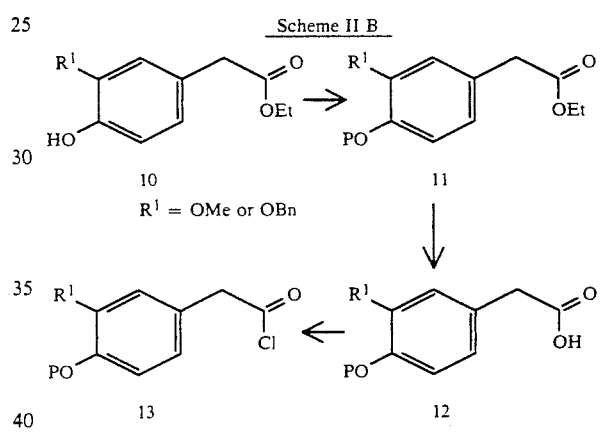

Scheme I

According to reaction scheme I, compounds of Formula 1 (wherein $R^3$ and $R^4$ are independently selected from $C_1$-$C_4$-alkyl, $C_1$-$C_4$-alkoxy, benzyloxy, $C_1$-$C_4$-alkylthio, halogen, halo-$C_1$-$C_4$-alkyl and nitro Aldrich Chemical Company, Milwaukee, Wis., or straightforward modifications thereof, are converted to the corresponding cyanohydrins by treatment with a cyano derivative such as trimethylsilyl cyanide, preferably in the presence of a catalytic amount of lithium cyanide, and the cyanohydrins are reduced to the amino alcohols of Formula 3 by treatment with a suitable reducing agent such as LAH or borane or by catalytic hydrogenation using a suitable catalyst, for example Raney nickel. The compounds of Formula 3 are further treated with a dehydrating agent, for example a Br onsted acid or a Lewis acid, preferably hydrochloric acid, to afford the compounds of Formula 4, wherein m is 0 when n is 1, m is 1 when n is 2 and m is 2 when n is 3. The compounds of Formula 3 and Formula 4 are key intermediates used in the synthesis of the compounds of formula (I).

Scheme II

According to reaction scheme II A, compounds of Formula 5 (Aldrich Chemical Company, Milwaukee, Wis., or straightforward modifications thereof) are treated with chlorosulfonic acid to afford the compounds of Formula 6. The compounds of Formula 6 are, in turn, treated with a suitable reducing reagent, for example, a metal in the presence of an acid, preferably zinc/sulfuric acid, to afford the thiol compounds of Formula 7. The compounds of Formula 7 are then alkylated using standard methods, for example, they are treated with methyl iodide in the presence of a suitable base such as potassium carbonate, to afford the compounds of Formula 8. The compounds of Formula 8 are converted to the compounds of Formula 9 by treatment with a suitable halogenating agent, for example, oxalyl chloride or thionyl chloride. The compounds of Formula 9 are key intermediates used in the synthesis of the compounds of formula (I).

According to reaction scheme II B, compounds of Formula 10 (Aldrich Chemical Company, Milwaukee, Wis., or straightforward modifications thereof) are treated with a suitable reagent for protecting the phenolic hydroxyl group, for example, benzyl bromide in the presence of a suitable base, such as potassium carbonate, to afford compounds of Formula 11. Compounds of Formula 11 are hydrolyzed to the corresponding carboxylic acids of Formula 12 in either basic or acidic solution, preferably by treatment with aqueous base such as lithium hydroxide. The carboxylic acid is then treated with a suitable chlorinating agent, such as oxalyl chloride or thionyl chloride, to afford the compounds of Formula 13. The compounds of Formula 13 are key intermediates used in the synthesis of the compounds of formula (I).

compounds of Formula 15 (wherein m is 0, 1 or 2) by treatment with a suitable acid, such as, methanesulfonic acid. The compounds of Formula 15 are key intermediates used in the synthesis of the compounds of formula (I).

Scheme IV

According to reaction scheme IV, a compound of Formula 4·(wherein m is 0, 1 or 2) is condensed with a

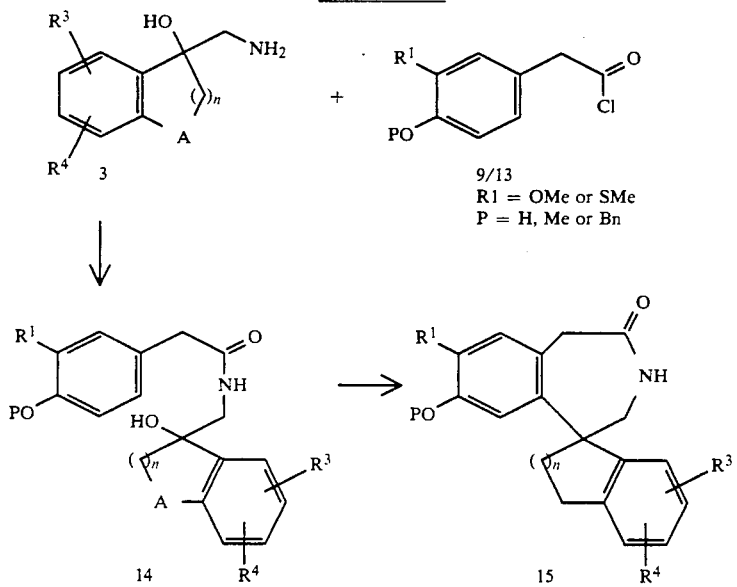

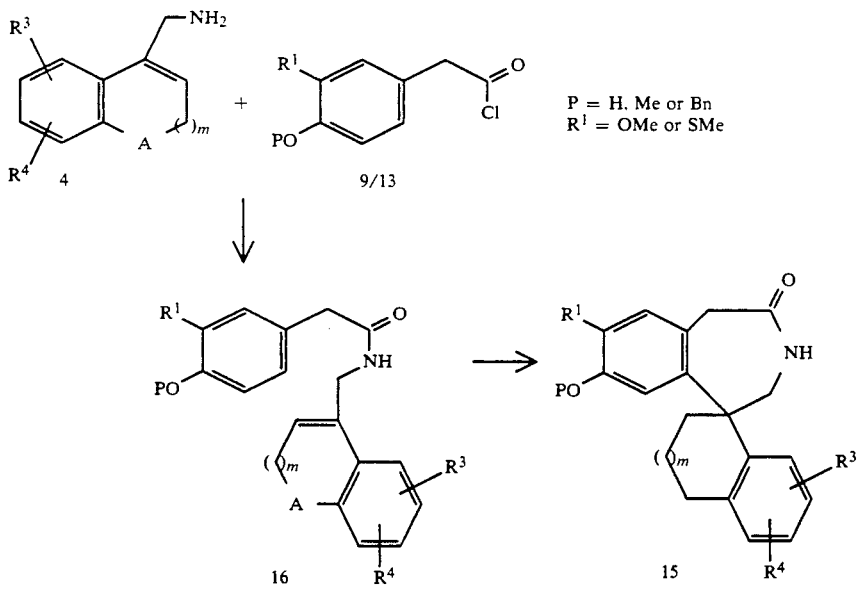

Scheme III

According to reaction scheme III, a compound of Formula 3 is condensed with a compound of Formula 9 or Formula 13 in the presence of a suitable acid acceptor, for example sodium bicarbonate, to afford a compound of Formula 14. The compounds of Formula 14, wherein A is —CH$_2$—, are, in turn, cyclized to the compound of Formula 9 or Formula 13 in the presence of a suitable base such as sodium bicarbonate to afford a compound of Formula 16. The compounds of Formula 16 (wherein A is —CH$_2$—) are, in turn, converted to the compounds of Formula 15 by treatment with a suitable acid, for example, methanesulfonic acid. The compounds of Formula 15 are key intermediates used in the synthesis of the compounds of formula (I).

amination using a suitable aldehyde in the presence of a suitable reducing agent to afford the compounds of Scheme V

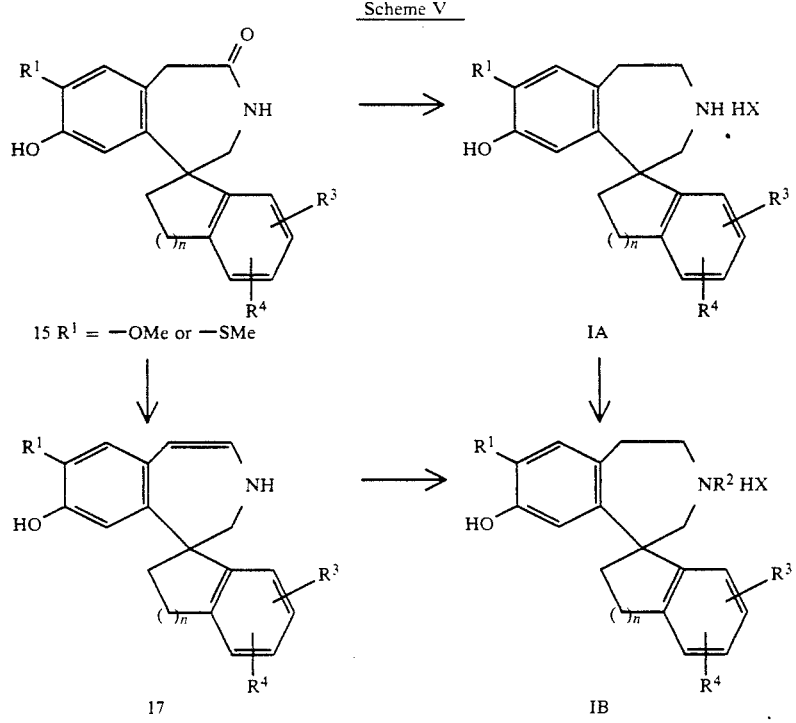

Scheme VI

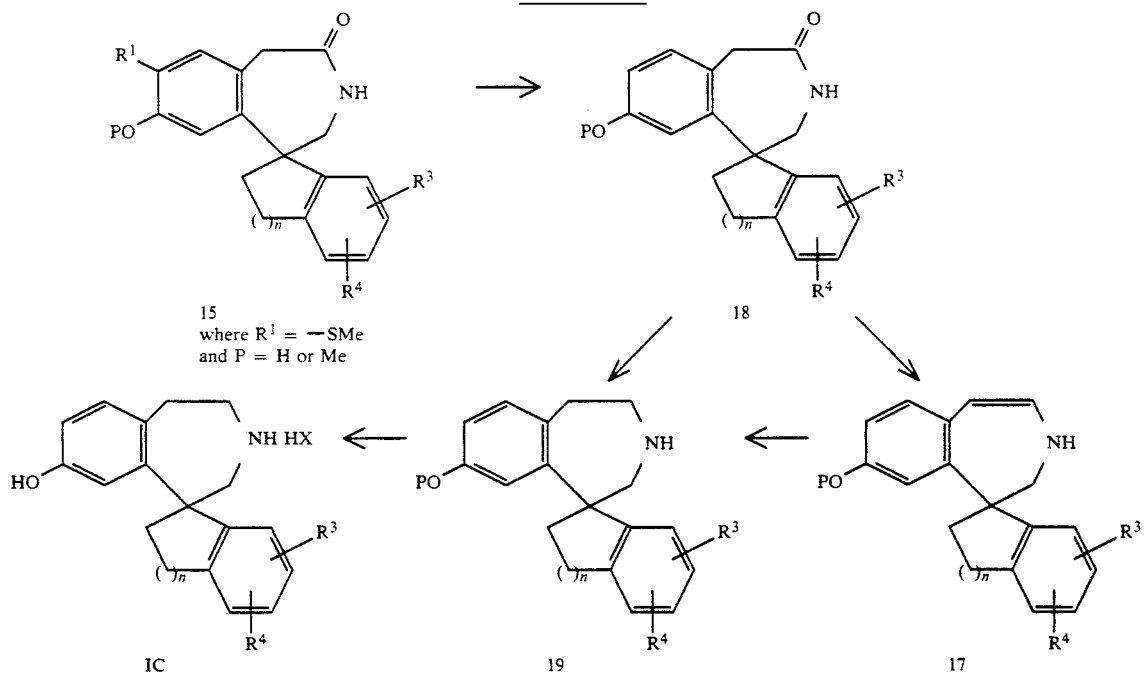

Scheme V

According to reaction scheme V, compounds of Formula 15 (wherein R¹ is hydrogen) are treated with a suitable reducing agent for reducing the lactam directly to the cyclic amine, for example lithium aluminum hydride, to afford compounds of Formula I A. The compounds of Formula I A are N-alkylated by reductive amination using a suitable aldehyde in the presence of a suitable reducing agent to afford the compounds of Formula I B. For example, the N-methyl compound is prepared by treating a compound of Formula I A with formaldehyde and sodium cyanoborohydride. Alternately, the compounds of Formula 15 are treated with a suitable reducing agent for converting the lactam to the corresponding enamine compounds, for example borane, to afford the compounds of Formula 17. The compounds of Formula 17 are, in turn N-alkylated by reductive amination using a suitable aldehyde in the presence of a suitable reducing agent to afford the compounds of Formula I B.

Scheme VI

According to reaction scheme VI, compounds of Formula 15 in which $R^1$ is -SMe are treated with Raney nickel to afford compounds of Formula 18. The compounds of Formula 18 are, in turn, reduced to the enamines of Formula 17 and subsequently to the compounds of Formula 19 by sequential treatment with suitable reducing agents as discussed above in reaction scheme V, or they are reduced directly to the compounds of Formula 19 by treatment with a suitable reducing agent such as lithium aluminum hydride. The compounds of Formula 19 are treated with a reagent for removing the protecting group when P is not hydrogen to afford the compounds of Formula I C. For example when P is methyl a preferred method for removing P is by treatment with boron tribromide.

Scheme VII

According to reaction scheme VII, compounds of Formula 15 are reduced with a suitable reducing agent to the corresponding 2,3,4,5-tetrahydro-1H-3-benzazepine compound and then deprotected using standard methods, preferably by treatment with boron tribromide, to afford the catechol compounds of Formula 1 D. Compounds of Formula 15 are converted to the N-alkyl compounds of Formula I E by sequential reduction of the lactam, as described above, to afford the enamines of formula 17, treatment with an appropriate aldehyde in the presence of sodium cyanoborohydride (reductive amination) and finally deprotection of the catechol hydroxyl groups, preferably by treatment with boron tribromide. Alternately, the compounds of Formula 17 are reduce to afford the compounds of formula 20 or, the compounds of formulas 17 are converted to the N-alkyl compounds of Formula 19 by the alkylation procedure described in reaction scheme VII.

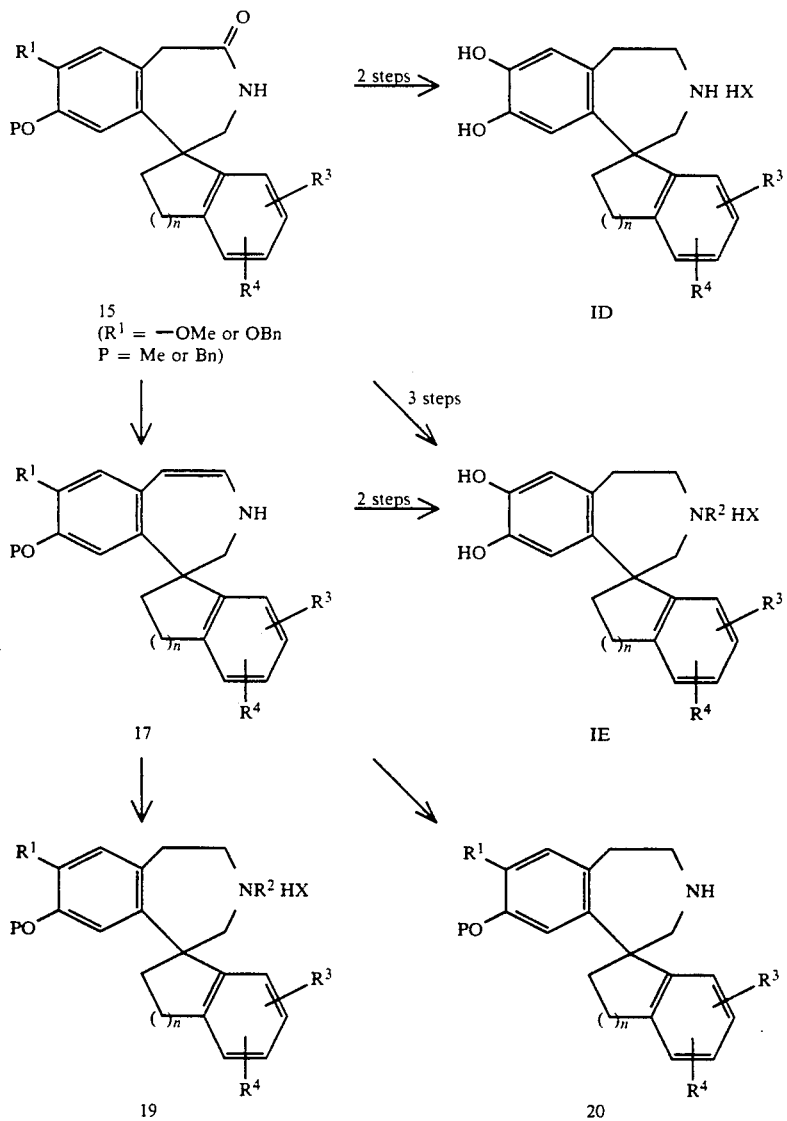

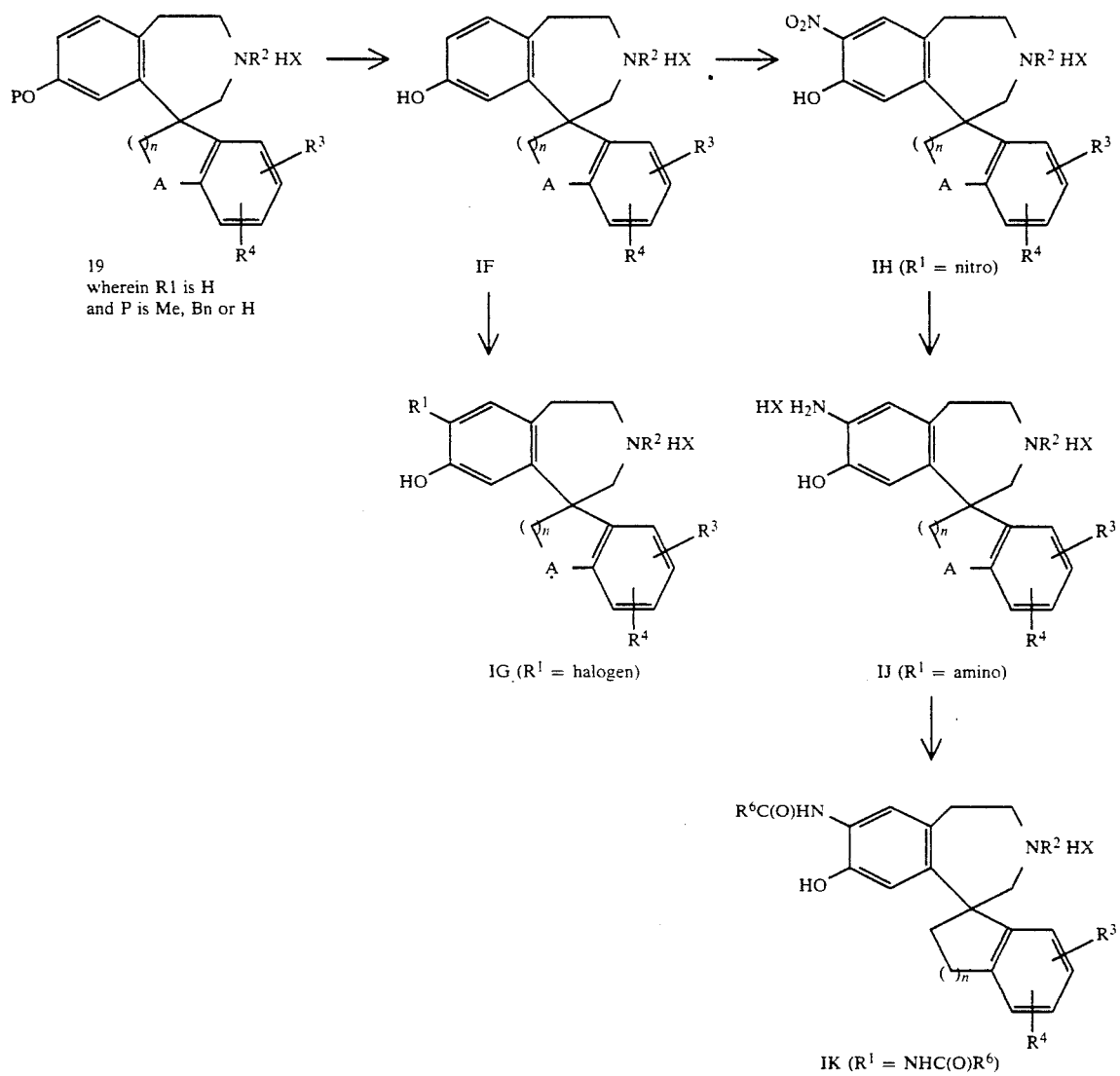
Scheme VIII A
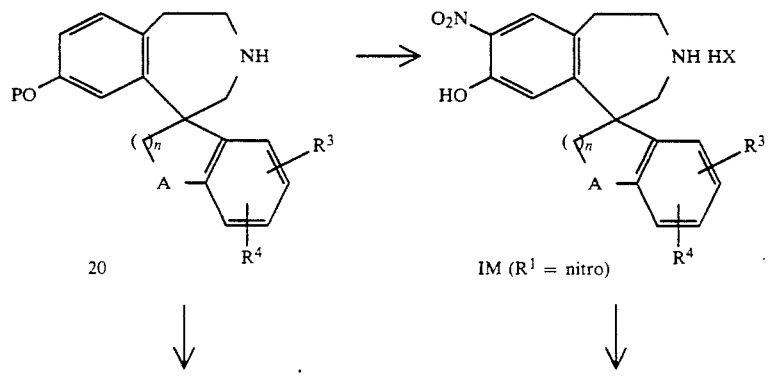
Scheme VIII B

Scheme VIII B

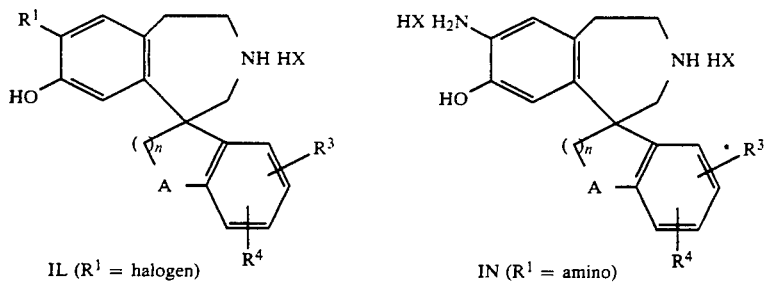

IL ($R^1$ = halogen)  IN ($R^1$ = amino)

Scheme VIII

According to reaction scheme VIII A, the compounds of Formula 19 (wherein $R^1$ is H) are treated with a suitable reagent for removing the phenol-protecting group to afford the compounds of formula I F. The compounds of Formula I F are halogenated by treatment with a suitable halogenating agent, for example bromine in the presence of a suitable acid such as formic acid, to afford the compounds of Formula I G. The compounds of Formula I F are nitrated by standard methods, for example by treatment with a mixture of nitric and acetic acids, to afford the compounds of Formula I H. The compounds of Formula I H are, in turn, treated with a suitable reducing agent, for example lithium aluminum hydride, to afford the amino compounds of Formula I J. The compounds of Formula I J are further treated with with suitable reagent for acetylating the amine such as acetyl chloride, preferably in the presence of a base such as sodium bicarbonate or triethylamine to afford the compounds of Formula I K.

According to reaction scheme VIII B, the compounds of Formula 20 (wherein $R^1$ is H) are converted to the corresponding halo, nitro and amino compounds of Formulas I L, I M and I N, respectively as described above in this scheme for the preparation of the halo, nitro and amino compounds of Formula I G, I H and I J, respectively, from the compounds of Formula 19.

Scheme IX A

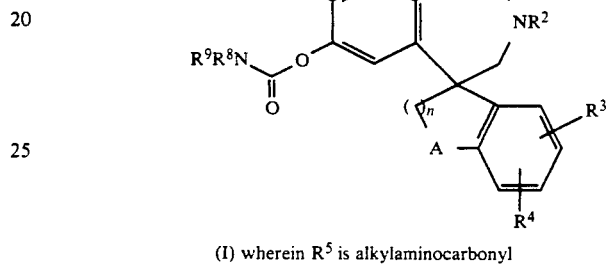

(I) wherein $R^5$ is H

-continued
Scheme IX A (I) wherein $R^5$ is alkylaminocarbonyl

Scheme IX B (I) wherein $R^5$ is H (I) wherein $R^5$ is alkanoyl

Scheme IX

According to reaction scheme IX A, compounds of formula (I) in which $R^5$ is hydrogen and neither of $R^3$ or $R^4$ is hydroxy are converted to carbamoyl derivatives of the phenolic hydroxyl group. Methods for the preparation of carbamoyl derivatives of phenols are well known in the art. For example, several methods for preparing carbamoyl derivatives of 8-hydroxy-1-phenyl-2,3,4,5-tetrahydro-1H-3-benzazepines are described in U.S. Pat. No. 4,284,555, incorporated herein by reference.

According to reaction scheme IX B, compounds of formula (I) in which $R^5$ is hydrogen and neither of $R^3$ or $R^4$ is hydroxy are converted to prodrug ester or carbonate derivatives (compounds of formula (I) in which $R^5$ is alkanoyl). Methods for the preparation of phenolic esters and phenolic carbonate derivatives are well known in the art. For example, several methods for preparing ester and carbonate derivatives of 8-hydroxy-1-phenyl-2,3,4,5-tetrahydro-1H-3-benzazepines are described in U.S. Pat. No. 4,477,378, incorporated herein by reference.

with an easily removable protecting group such as methoxymethoxy, affording a compound of Formula 22. The compound of Formula 22 is, in turn, treated with a suitable base, for example, butyllithium, followed by carbon dioxide to afford a compound of Formula 23. The compound of Formula 23 is then treated with a suitable reagent for removing both the amino-protecting group and the phenol-protecting group simultaneously, for example, in the case of the t-Boc and MOM protecting groups, a suitable mild acid, to afford a compound of Formula I P as the acid addition salt of the

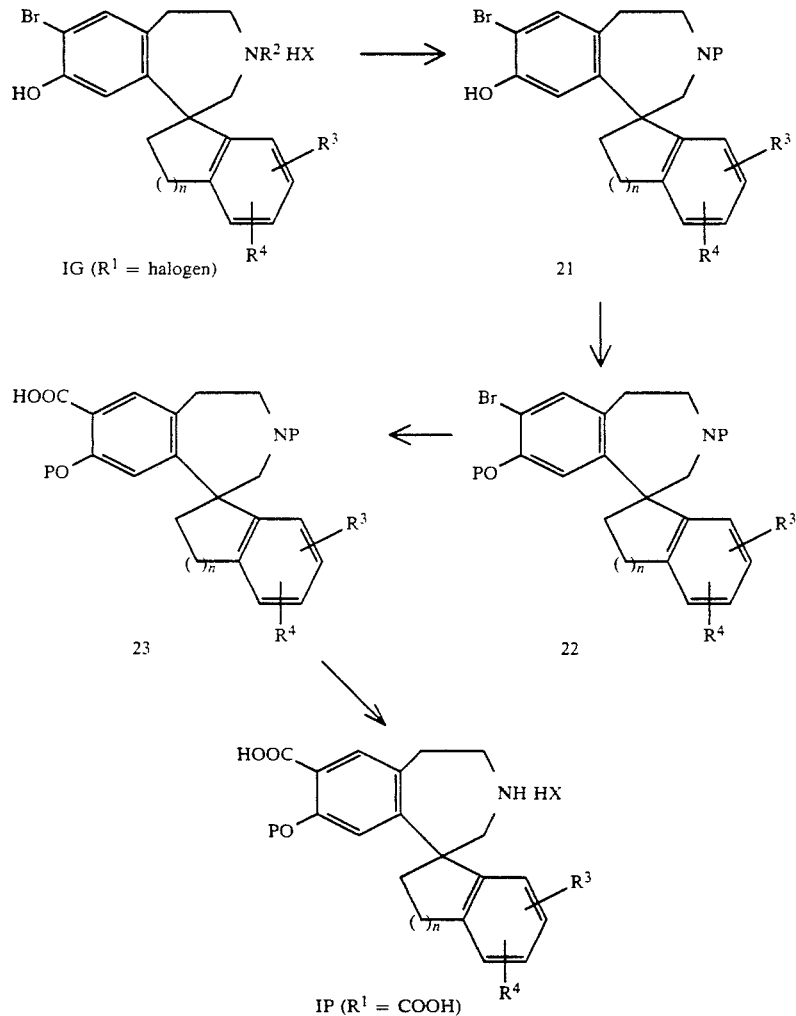

Scheme X

Scheme X

According to reaction scheme X, a halo-substituted compound of Formula I G is treated with a suitable reagent for protecting the amino group, with for example, a t-butyloxycarbonyl (t-Boc) group to afford a compound of Formula 21. The amino-protected compound of Formula 21 is then treated with a suitable reagent for protecting the phenolic oxygen, for example amine. The carboxy-compound ($R^1$=COOH) may then be converted by standard procedures (see, for example J. March, *Advanced Organic Chemistry: Reactions, Mechanisms and Structure*, Wiley-Interscience, 1985) into the compounds of Examples 143 (esterification), 144 (alkylation), 145 (alkylation), 146 (reduction), 147 (reduction/alkylation), 148 (reduction), 149 (conversion to amide) and 150 (conversion to amide/reduction).

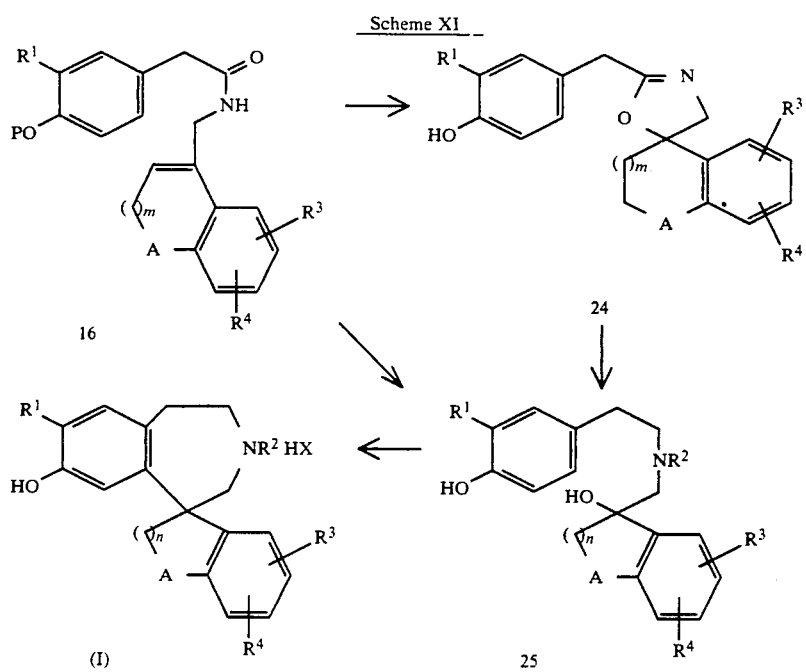

Scheme XI

According to reaction scheme XI, compounds of Formula 16 are cyclized by treatment with a suitable acid, for example, methanesulfonic acid, to afford the compounds of Formula 24. Compounds of Formula 24 are treated with a suitable reducing agent, such as borane to afford the compounds of Formula 25. The compounds of Formula 25, in turn, are cyclized with a suitable acid, for example, methanesulfonic acid, to afford compounds of Formula (I).

The term "addictive behavior" is used herein to mean symptoms and maladaptive behavioral changes associated with periodic or continued use of psychoactive substances. These behavioral changes, for example, continued compulsive use of the psychoactive substance despite the presence of persistent or recurrent social, occupational, psychological or physical problems that the person knows are caused by or may be exacerbated by continued use of the substance, would be viewed as extremely undesirable in almost all cultures.

The term "affective disorder" as used herein refers to disorders that are characterized by changes in mood as the primary clinical manifestation, for example, major depression.

The term "antipsychotic agent" as used herein refers to drugs used extensively in the symptomatic management of all forms of schizophrenia, organic psychosis, the manic phase of manic depressive illness and other acute idiopathic illnesses and occasionally used in depression or in severe anxiety.

The term "attention deficit disorder" refers to a recently classified pediatric neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the cognitive (information processing) functions of perceiving, thinking and remembering, such as, for example, dementia and cognitive impairment due to organic brain disease related directly to alcoholism.

The term "dopamine-related neurological disorders" as used herein refers to behavioral disorders, such as psychoses and addictive behavior disorders; affective disorders, such as major depression; and movement disorders such as seizure disorders, Huntington's Disease and Gilles de la Tourette's syndrome; which have been linked, pharmacologically and/or clinically, to excessive functional dopaminergic activity in the CNS.

The term "seizure disorders" is used as defined in the seventh edition of Goodman and Gilman's *The Pharmacological Basis of Therapeutics*. Seizures are sudden and transitory episodes of abnormal phenomena of motor (convulsion), sensory, autonomic or psychic origin. Seizure disorders for which no cause can be identified are commonly called primary or idiopathic epilepsy. Secondary or symptomatic epilepsy designates seizure disorders associated with such factors as trauma, neoplasm, infection, developmental abnormalities, cerebrovascular disease or various metabolic conditions.

Competitive Binding

Dopamine produces biological responses through stimulation of its receptors on cell membranes. For the purpose of identifying compounds as dopamine antagonists which are capable of interacting with dopamine receptors, a ligand-receptor binding assay was carried out as an initial screen.

D-1 and D-2 Receptor Binding Assays

Homogenized rat caudate was incubated in the presence of [$^{125}$I]SCH-23982 (a selective antagonist of the dopamine D-1 receptor) and the compounds of this invention, according to procedures described by A. Sidhu, et al. in *European J Pharmacology*, 1985, 113: 437 and in *European J Pharmacology*, 1986, 128: 213. The compounds compete with the radiolabeled ligand for occupancy of the receptors and the molar potency of each compound was quantified. The affinity of the compound for the receptor ($K_i$) was calculated as described by Y. C. Cheng and W. H. Prusoff in *Biochemical Pharmacology*, 1973, 22: 3099 from the relationship $K_i = IC_{50}(1+[L]/K_D)$ where $IC_{50}$ is the concentration of test compound which produces a 50% inhibition in the specific binding of the radioligand, L; [L] is the concentration of radioligand; and $K_D$ is the affinity of the radioligand for the receptor.

The procedure for the dopamine D-2 receptor binding assay was similar to that used for the D-1 receptor assay. Homogenized rat caudate was the source of the D-2 receptors. The tissue homogenate was incubated in the presence of [$^3$H]-spiperone (a selective antagonist of the dopamine D-2 receptor) and the compounds being evaluated, according to the protocol described by E. A. Frey, T. E. Cote, C. W. Grewe and J. W. Kebabian in *Endocrinology*, 1982, 110, 1897. The molar affinity of the compound for the receptor binding site was calculated by the same method used for the D-1 receptor assay, assuming a competitive interaction between the compound and the radiolabeled ligand.

The competitive binding data ($K_i$ values) from the D-1 and D-2 receptor binding assays are shown in Table 1. The $K_i$ values are inversely proportional to the affinity of the compound for the receptor, therefore it is apparent that the compounds of the invention have high affinity for dopamine D-1 receptors.

TABLE 1

| Competitive Binding for D-1 and D-2 Receptors | | |
| --- | --- | --- |
| Example # | D-1 $K_i$ ($\mu$M) | D-2 $K_i$ ($\mu$M) |
| 9 | 2.61 | >100 |
| 10 | 0.05 | 562 |
| 11 | 0.11 | 6.8 |
| 13 | 15.9 | >100 |
| 14 | 0.41 | >100 |
| 15 | 0.65 | >100 |
| 16 | 0.33 | 5.5 |
| 17 | 0.31 | 18.0 |
| 18 | 0.01 | 5.9 |
| 21 | 1.32 | 39.2 |
| 24 | 0.81 | >100 |
| 25 | 0.16 | 9.5 |
| 26 | 16.2 | >100 |
| 27 | 0.84 | >100 |
| 28 | 23.0 | 136 |
| 29 | 0.44 | 112 |
| 30 | 0.68 | 14.6 |
| 31 | 0.03 | 10.1 |
| 32 | 1.5 | 112 |
| 33 | 3.41 | 8.8 |
| 34 | 8.0 | 4.2 |
| 35 | 0.94 | 7.5 |
| 135 | 0.16 | 0.66 |
| 136 | 1.67 | >100 |
| 137 | 0.02 | >100 |
| 138 | 2.08 | >100 |
| dopamine | 6.73 | 0.554 |

Functional Assays

The interaction of dopamine or a dopamine D-1 receptor agonist with the D-1 receptor causes a dose-dependent increase in the adenylate cyclase-catalyzed conversion of adenosine triphosphate (ATP) to cyclic adenosine monophosphate (cAMP). The functional activity of a compound was determined by assaying, in vitro, its ability to either stimulate the enzyme adenylate cyclase to produce more cAMP (agonist activity) or to antagonize a dopamine-induced increase in cAMP levels. The protocol for the adenylate cyclase assays was described by K. J. Watling and J. E. Dowling in *J Neurochemistry*, 1981, 36: 599 and by J. W. Kebabian, et al. in *Proc Natl Acad Sci, USA*, 1972, 69: 2145. In order to determine agonist activity, cell-free tissue homogenates are incubated in an ionic buffer solution containing ATP and the compound being evaluated. The tissue was obtained from either goldfish retina or rat striatum.

In order to determine functional antagonist activity, these assays were repeated in the presence of 10 $\mu$M dopamine and increasing concentrations of the compound being evaluated. The results of the assays for antagonist activity are shown in Table 2. The $K_i$ values were calculated as described by Y. C. Cheng and W. H. Prusoff in *Biochemical Pharmacology*, 1973, 22, 3099 from the relationship $K_i = IC_{50}([S]/K_D)$. The applicability of this relationship is based on the assumption that tissues used in the assay do not have large receptor reserves for the D-1 and D-2 receptors. In this expression $IC_{50}$ is defined as the concentration of test compound which produces a 50% reduction in the response to an agonist, S; [S] is the concentration of agonist in the assay; and $K_D$ is the affinity of the agonist for the receptor.

TABLE 2

| D-1 Antagonist Activity in Adenylate Cyclase Assay | | |
| --- | --- | --- |
| Example # | $K_i$ ($\mu$M) | IC50 |
| 9 | 2.73 | 15.7 |
| 10 | 0.06 | 0.32 |
| 11 | 0.04 | 0.23 |
| 14 | 0.10 | 0.58 |
| 16 | 0.09 | 0.51 |
| 17 | 0.14 | 0.83 |
| 18 | 0.01 | 0.05 |
| 21 | 0.24 | 1.38 |
| 24 | 0.13 | 0.53 |
| 25 | 0.02 | 0.13 |
| 27 | 0.40 | 2.29 |
| 29 | 0.74 | 4.24 |
| 30 | 0.16 | 0.92 |
| 31 | 0.02 | 0.14 |
| 32 | 0.56 | 3.24 |
| 135 | 0.17 | 0.96 |
| 136 | 0.75 | 4.34 |
| 137 | 0.03 | 0.14 |
| 138 | 0.51 | 2.93 |

Table 2 shows that the compounds of the invention are potent antagonists of the dopamine receptor-mediated adenylate cyclase-catalyzed conversion of adenosine triphosphate (ATP) to cAMP and, therefore, prevent the physiological effects of excessive stimulation of dopamine D-1 receptors.

Rotation Behavior

The behavioral assay used herein was based on the rat rotational model. Striatal dopamine was depleted by the intracranial injection of 6-hydroxydopamine, a neurotoxin which specifically destroys catecholaminergic neurons. The intracranial injection was conducted on anesthetized animals using standard stereotaxic techniques (U. Ungerstedt and G. W. Arbuthnott, *Brain Research*, 1970, 24: 485 and U. Ungerstedt, Acta *Physiol. Scand. Suppl.*, 1973, 367, 69:). This unilateral lesioning of dopamine-containing neurons causes the post synaptic dopamine receptors to become supersensitive to dopaminergic stimulation in behavioral assays. When these striatal dopamine receptors are stimulated by dopamine agonists, the rats rotate or physically turn, in a direction that is away from the side of their body that receives the greater dopaminergic activation due to the receptor supersensitivity. Antagonist activity was measured by the ability of the test compound to block rotation induced by stimulation by A-68930, a selective dopamine D-1 agonist (J. W. Kebabian, C. Briggs, D. R. Britton, K. Asin, M. DeNinno, R. G. MacKenzie, J. F. McKelvy and R. Schoenleber, *Am. J. Hypertension*, 1990, 3:40S–42S). The dose of agonist was 1.0 μmol/kg administered subcutaneously

TABLE 3

| Number of Rotations in Two Hours | | | |
|---|---|---|---|
| Dose of Example 18 (μmol/kg)* | Number of Rotations/2 h | Dose of Example 27 (μmol/kg)* | Number of Rotations/2 h |
| saline | 1118 | saline | 1011 |
| 3.2 | 491 | 3.0 | 913 |
| 10.0 | 412 | 10.0 | 652 |
| 32.0 | 154 | 30.0 | 119 |

*injected subcutaneously

Table 3 shows that the compounds of the present invention are active in vivo and block the dopamine D-1 agonist-induced rotation behavior of rats.

As used herein, the term "pharmaceutically-acceptable auxillaries" means non-toxic, inert, solid, semi-solid or liquid fillers, diluents, encapsulating materials or formulation carriers or adjuvants of any type. Some examples of the materials that can serve as pharmaceutically-acceptable auxillaries are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically-acceptable antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically-effective amount" of the dopaminergic agent is meant a sufficient amount of the compound to treat neurological, psychological or behavior disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The total daily dose of the compounds of the present invention administered to a host in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day administered in either multiple doses or in a single dose.

The compounds of the present invention may be administered individually or in combinations or in concurrent therapy with other agents which affect the central or peripheral nervous system. The compounds of the present invention may also be co-administered with agents, for example enzyme inhibitors, which block their metabolic transformation outside the CNS.

Liquid dosage forms for oral administration may include pharmaceutically-acceptable emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as solvents or suspending media. For this purpose any bland fixed oil can be employed including synthetic mono- or diglycerides. In addition, fatty acids such as oleic acid are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms may also be made by forming microcapsule matrices of drugs and biodegradable polymers such as polyactide-polyglycolide. Depending on the ratio of drug to polymer and the composition of the polymer, the rate of drug release may be controlled. Examples of other biodegradable polymers include poly-orthoesters and polyanhydrides. The depot injectables may also be made by entrapping the drug in liposomes or microemulsions which are compatible with body tissues.

Suppositories for rectal administration of the drug may be prepared by mixing the drug with a suitable nonirritating excipient, such as cocoa butter or polyethylene glycol, which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills may additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically-acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients such as lactose, talc, silicic acid, aluminum hydroxide, calcium silicates and polyamide powder, or mixtures of these substances. Sprays may additionally contain customary propellants such as chlorofluorohydrocarbons, or acceptable non-halogenated propellants.

Transdermal patches have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate controlling membrane or by dispersing the compound in a polymer matrix or gel.

The foregoing may be better understood by reference to the following examples which are provided for illustration and not limitation of the invention.

EXAMPLE 1

1-Aminomethyl-1-hydroxy-indan

Step 1: 1-Cyano-1-(trimethylsilyloxy)-indian

To a solution of 1-indanone (20 g, 150 mmole) in 200 mL of tetrahydrofuran (THF) was added lithium cyanide (10 mL of a 0.5M solution in DMF, 5 mmol, 0.03 equivalent). The reaction mixture was stirred for 5 minutes at ambient temperature and trimethylsilyl cyanide (30 g, 300 mmol, 2 equivalents) was added in one portion. The reaction mixture was stirred for 16 hours at ambient temperature and then concentrated under reduced pressure to give the title compound as a light brown oil. The crude product was carried on to the next step without purification.

Step 2: 1-Aminomethyl-1-hydroxy-indan

To a suspension of lithium aluminum hydride (12.8 g, 340 mmol, 2.25 equivalents) in 100 mL of refluxing THF, under nitrogen atmosphere, was added dropwise over a period of 35 minutes the product of Step 1. After the addition was complete, the reaction mixture was refluxed for 3.5 hours. The reaction mixture was then diluted with THF and the reaction was quenched by the addition of excess sodium sulfate decahydrate. The solids were removed by filtration through Celite® filter aid and washed with hot THF. The combined filtrates were concentrated to give the title compound as a yellow oil; $^1$H NMR (CD$_3$OD) δ 3.00–3.19 (m, 6H), 7.13–7.25 (m, 4H).

EXAMPLE 2

1-Aminomethyl-1-indene hydrochloride

To a stirred 2M solution of hydrogen chloride in isopropyl alcohol (200 mL) is added 10 g (61.3 mmol) of 1-aminomethyl-1-hydroxyindan, the product of Example 1. The resulting turbid suspension was refluxed for 6 hours and then concentrated under reduced pressure until a thick slurry formed. The slurry was diluted with diethyl ether and filtered. The solid was dried to give 8.0 g (73% yield from Step 1 of Example 1) of the title compound as a pale yellow powder; $^1$H NMR (CD$_3$OD) δ 3.49 (m, 2H), 4.15 (m, 2H), 6.67 (t, 1H, J=2 Hz), 7.3 (m, 2H), 7.47 (m, 2H).

EXAMPLE 3

4-Methoxy-3-(methylthio)phenylacetyl chloride

Step 1: 3-Chlorosulfonyl-4-methoxyphenylacetic acid

Chlorosulfonic acid (300 mL) was cooled to −10° C. and a solution of 4-methoxyphenylacetic acid (100 g, 0.6 mole) in methylene chloride (300 mL) was added dropwise over a period of 40 minutes. After the addition was complete, cooling was discontinued and the reaction mixture was stirred at ambient temperature for 18 hours. The reaction mixture was then poured slowly over 4 L of crushed ice. The resultant precipitate was filtered and dissolved in THF. The THF solution was dried over anhydrous magnesium sulfate, filtered and concentrated to give a pale yellow solid. The solid was triturated with THF/petroleum ether (b.p. 30°-60° C.) and filtered to give 125 g (79% yield from 1-indanone) of the title compound as a white crystalline solid; DCI MS M/Z: 282 (M+NH$_4$)$^{30}$; $^1$H NMR (CD$_3$OD) δ 3.67 (s, 2H), 4.02 (s, 3H), 7.30 (d, 1H, J=9 Hz), 7.69 (dd, 1H, J=9, 3 Hz), 7.85 (d, 1H, J=3 Hz).

Step 2: 4-Methoxy-3-thiophenylacetic acid

Zinc dust (140 g, 2.0 mol, 5.4 equivalents) was added in one portion with stirring to a mixture of concentrated sulfuric acid (280 g) and ice (820 g) at −5° C. To the resulting slurry, at −5° C., was added 3-chlorosulfonyl-4-methoxyphenylacetic acid (100 g, 0.38 mol), from Step 1, in portions over a period of 5 minutes. After the addition was complete, cooling was discontinued and the reaction mixture was stirred at ambient temperature for 2 hours. The reaction mixture was then warmed to 90° C. over 50 minutes and stirred at 90° C. for 2 hours. The resulting slurry was cooled to 0° C. and the solids were filtered. The filter cake was added to THF and zinc was separated by filtration. The filtrate was dried over anhydrous magnesium sulfate, filtered and concentrated to give 38 g (50% yield) of the title compound as a white solid; $^1$H NMR (CD$_3$OD) δ 3.46 (s, 2H), 3.25 (s, 3H), 6.85 (d, 1H, J=8.7 Hz), 6.99 (dd, 1H, J=8.7, 2.7 Hz), 7.40 (d, 1H, J=2.7 Hz).

Step 3: 4-Methoxy-3-(methylthio)phenylacetic acid

To a suspension of 4-methoxy-3-thiophenylacetic acid (1.61 g, 81 mmol) in acetone was added potassium carbonate (56 g, 400 mmol, 5 equivalents), followed by methyl iodide (11.5 g, 81 mmol, 1 equivalent). After stirring at ambient temperature for 5.5 hours, 2N aqueous hydrochloric acid solution (400 mL) was slowly added. The resulting solution was then extracted with 2×200 mL of THF/diethyl ether (1:1) followed by diethyl ether (400 mL). The combined organic layers were washed with 2×250 mL of 10% aqueous sodium thiosulfate and 250 mL of saturated aqueous sodium chloride solution (brine), dried over anhydrous magnesium sulfate, filtered and concentrated to give 56 g (96% yield) of the title compound as a pale yellow solid; DCI MS M/Z: 230 (M+NH$_4$)$^+$; $^1$H NMR (CD$_3$OD) δ 3.36 (s, 3H), 3.53 (s, 2H), 3.82 (s, 3H), 6.83 (d, 1H, J=8.7 Hz), 7.02 (dd, 1H, J=8.7, 2.7 Hz), 7.06 (d, 1H, J=2.7 Hz).

Step 4: 4-Methoxy-3-(methylthio)phenylacetyl chloride

To a solution of 4-methoxy-3-(methylthio)phenylacetic acid (10.2 g, 47.3 mmol) in THF (300 mL) was added oxalyl chloride (6.6 g, 52 mmol, 1.1 equivalent) followed by a catalytic amount of N,N-dimethylformamide (DMF) (∼0.5 mL). The reaction mixture was stirred at ambient temperature for 3 h and then concentrated under reduced pressure to give the title compound as a yellow oil. The product was used without purification.

EXAMPLE 4

4-Benzyloxy-3-methoxyphenylacetyl chloride

Step 1: Ethyl 4-benzyloxy-3-methoxyphenylacetate

To a solution of ethyl 4-hydroxy-3-methoxyphenylacetic acid (25 g, 120 mmol), commercially available from Aldrich Chemical Company, in acetone (150 mL) was added potassium carbonate (50 g, 360 mmol) followed by benzyl bromide (23 g, 130 mmol). The reaction mixture was stirred at ambient temperature for 15 hours and then was concentrated under reduced pressure. The residue was partitioned between 500 mL of water and 500 mL of diethyl ether. The aqueous layer was extracted with 300 mL of diethyl ether and the combined organic layers were dried over anhydrous magnesium sulfate, filtered and concentrated to give 32 g of the title compound as a yellow solid. The product was carried on to the next step without purification.

Step 2: 4-Benzyloxy-3-methoxyphenylacetic acid

To a solution of ethyl 4-benzyloxy-3-methoxyphenylacetate (32 g, 110 mmol), from Step 1, in ethanol (200 mL) and THF (20 mL) was added 200 mL of a 1M aqueous lithium hydroxide solution. The resulting mixture was stirred at ambient temperature for 4 hours and then 1M aqueous hydrochloric acid solution was added to precipitate the product. The solid was filtered, washed with water, taken up in diethyl ether, dried over anhydrous magnesium sulfate, filtered and concentrated under reduced pressure to give the title compound as a yellow solid. The solid was recrystallized from methylene chloride/petroleum ether (b.p. 30°-60° C.) to give 19 g (58% yield based on ethyl 4-hydroxy-3-methoxyphenylacetic acid) of the title compound as a white solid; $^1$H NMR (CDCl$_3$) δ 3.57 (s, 2H), 3.88 (s, 3H), 5.14 (s, 2H), 6.74 (dd, 1H, J=8.0, 2.7 Hz), 6.82-6.85 (m, 2H), 7.28-7.45 (m, 5H).

Step 3: 4-Benzyloxy-3-methoxyphenylacetyl chloride

To a solution of 4-benzyloxy-3-methoxyphenylacetic acid (5.0 g, 18 mmol), from Step 2, in THF (40 mL) was added oxalyl chloride (2.54 g, 20 mmol, 1.1 equivalent) followed by a catalytic amount of DMF (∼0.2 mL). The resulting mixture was stirred at ambient temperature for 2 hours and then concentrated under reduced pressure to give the title compound which was used without purification.

EXAMPLE 5

8-Hydroxy-7-methoxy-4-oxo-1-(spiro-1'-indan)-2,3,4,5-tetrahydro-1H-3-benzazepine Step 1: N-(4-Benzyloxy-3-methoxyphenylacetyl)-1-aminomethyl-1-hydroxyindan To a solution of 4-benzyloxy-3-methoxyphenylacetyl chloride (18 mmol), the product of Example 4, in 50 mL of methylene chloride was added 50 mL of saturated aqueous sodium bicarbonate solution, followed by a solution of 1-aminomethyl-1-hydroxyindan (3.15 g, 19 mmol), the product of Example 1, in 20 mL of methylene chloride. The resulting two-phase mixture was stirred vigorously at ambient temperature for 2 hours. The aqueous and organic phases were separated and the aqueous phase was extracted with methylene chloride (75 mL). The combined organic layers were washed with 100 mL of 1M aqueous hydrochloric acid solution, dried over anhydrous magnesium sulfate, filtered and concentrated to give a yellow oil. The oil was purified by flash chromatography on silica gel eluting with 1:1 ethyl acetate/methylene chloride to give 6.17 g (82% yield) of the title compound as a white solid; $^1$H NMR (CDCl$_3$).δ.1.96–2.08 (m, 1H), 2.18–2.28 (m, 1H), 2.67–2.80 (m, 1H), 2.87–2.98 (m, 1H), 3.29–3.37 (m, 2H), 3.53–3.65 (m, 3H), 3.88 (s, 3H), 5.16 (s, 2H), 5.80–5.88 (m, 1H), 6.71 (dd, 1H, J=8.7, 3.0 Hz), 6.79 (d, 1H, J=3.0 Hz), 6.85 (d, 1H, J=8.7 Hz), 7.10–7.47 (m, 9H).

Step 2:
8-Hydroxy-7-methoxy-4-oxo-1-(spiro-1'-indan)-2,3,4,5-tetrahydro-1H-3-benzazepine To a solution of N-(4-benzyloxy-3-methoxyphenylacetyl)-1-aminomethyl-1-hydroxyindan (6.17 g, 15 mmol), from Step 1, in 5 mL of methylene chloride was added 100 mL of methanesulfonic acid. The resulting solution was stirred at ambient temperature for 14 hours and then poured over 400 mL of crushed ice. The aqueous mixture was extracted with 2×200 mL of methylene chloride and the combined organic layers were washed with saturated aqueous sodium bicarbonate solution, dried over anhydrous magnesium sulfate, filtered and concentrated under reduced pressure to give a yellow oil. The oil was purified by flash chromatography on silica gel eluting with 1:1 ethyl acetate/methylene chloride to give 1.39 g (30% yield) of the title compound as a white solid; $^1$H NMR (CDCl$_3$) δ 2.22–2.34 (m, 1H), 2.45–2.55 (m, 1H), 3.02–3.10 (m, 2H), 3.36 (d, 1H, J=15 Hz), 3.63–3.73 (m, 2H), 3.84 (s, 3H), 4.09 (d, 1H, J=15 Hz), 6.31 (s, 1H), 6.66 (s, 1H), 6.77 (dd, 1H, J=7.5 Hz), 7.06–7.13 (m, 1H), 7.14–7.20 (m, 1H), 7.27 (d, 1H, J=7.5 Hz).

EXAMPLE 6

7,8-Dimethoxy-4-oxo-1-(spiro-1'-indan)-2,3,4,5-tetrahydro-1H-3-benzazepine

Step 1:
N-(3,4-Dimethoxyphenylacetyl)-1-aminomethyl-indene

To a stirred solution of 3,4-dimethoxyphenylacetyl chloride (5.46 g, 25.5 mmol), commercially available from Aldrich Chemical Company, in 150 mL of methylene chloride was added 150 mL of saturated aqueous sodium bicarbonate. To this vigorously stirred two-phase system was added 1-aminomethyl-1-indene hydrochloride (4.60 g, 25.5 mmol), the product of Example 2, and 30 mL of 1M aqueous sodium hydroxide solution. The two-phase reaction mixture was stirred vigorously at ambient temperature for 2 hours and then the layers were separated. The aqueous layer was extracted with 75 mL of methylene chloride. The combined organics were washed sequentially with 1M aqueous sodium hydroxide solution (50 mL), 1M aqueous hydrochloric acid solution (50 mL), water (50 mL) and brine (50 mL), dried over anhydrous magnesium sulfate, filtered and concentrated under reduced pressure to give the title compound as a white powder; $^1$H NMR (CDCl$_3$) δ 3.32 (m, 2H), 3.54 (s, 2H), 3.77 (s, 3H), 3.86 (s, 3H), 4.42 (m, 2H), 5.62 (bs, 1H), 6.23 (t, 1H, J=2 Hz), 6.78 (m, 3H), 7.28 (m, 4H)..

Step 2:
7,8-Dimethoxy-4-oxo-1-(spiro-1'-indan)-2,3,4,5-tetrahydro-1H-3-benzazepine To 20 mL of methanesulfonic acid at ambient temperature was added N-(3,4-dimethoxyphenylacetyl)-1-aminomethyl-indene (2.0 g, 5.85 mmol) from Step 1. The resulting red-brown solution was stirred at ambient temperature for 4 hours and then it was poured onto 50 g of ice. The resultant slurry was then extracted with 3×50 mL of methylene chloride. The combined organic layers were washed sequentially with 3×20 mL of water, 2×20 mL of 1M aqueous sodium hydroxide solution, 20 mL of water and 20 mL of brine, dried over magnesium sulfate, filtered and concentrated to a white solid. Trituration of the solid with a mixture of methylene chloride and hexanes, followed by filtration gave 1.6 g (80% yield) of the title compound as a white powder; $^1$H NMR (CDCl$_3$) δ 2.30 (m, 1H), 2.43 (m, 1H), 3.05 (m, 2H), 3.40 (dd, 1H, J=7.0, 15 Hz), 3.53 (d, 0.5H, J=7.0 Hz), 3.57 (m, 3.5H), 3.78 (d, 1H, J=15 Hz), 3.82 (s, 3H), 4.0 (d, 1H, J=15 Hz), 6.32 (s, 1H), 6.58 (s, 1H), 6.78 (d, 1H, J=7.5 Hz) 7.03 (m, 2H), 7.18 (tt, 1H, J=2, 7 Hz), 7.26 (d, 1H, J=7.5 Hz).

EXAMPLE 7

1-Aminomethyl-1-hydroxy-1,2,3,4-tetrahydronaphthalene

Step 1:
1-Cyano-1-trimethylsilyloxy-1,2,3,4-tetrahydronaphthalene

To a solution of 1,2,3,4-tetrahydronaphthalene-1-one (20 g, 140 mmol) in THF (150 mL) was added 6 mL of a 0.5M solution of lithium cyanide (3 mmol, 0.02 equivalent). The reaction mixture was stirred for ~2 minutes and then trimethylsilyl cyanide (25 g, 250 mmol, 1.8 equivalent) was added in one portion. The reaction mixture was stirred for 4.5 hours. Solvents and excess trimethylsilyl cyanide were removed under reduced pressure to give the title compound as a yellow oil. The oil was used in the next step without purification.

Step 2:
1-Aminomethyl-1-hydroxy-1,2,3,4-tetrahydronaphthalene

To a suspension of lithium aluminum hydride (12 g, 0.32 mol, 2.25 equivalents) in refluxing THF (150 mL), under a nitrogen atmosphere, was added, dropwise over a period of 30 minutes, a solution of 1-cyano-1-trimethylsilyloxy-1,2,3,4-tetrahydronaphthalene, from Step 1, in 150 mL of THF. The resulting mixture was refluxed for 4 hours and then cooled to ambient temperature and diluted with THF. Sodium sulfate decahydrate was added to quench the excess lithium aluminum hydride. The solids were filtered over Celite ® filter aid. The filtrate was then concentrated to give a light brown, waxy solid which was used in the next step without purification.

EXAMPLE 8

1-Aminomethyl-3,4-dihydronaphthalene

1-Aminomethyl-1-hydroxy-1,2,3,4-tetrahydronaphthalene, the product of Example 7, was refluxed in a 2N solution of hydrogen chloride in 2-propanol (250 mL) for 5 hours. A portion of the 2-propanol was removed under reduced pressure to give a slurry. Diethyl ether was added to precipitate the hydrochloride salt. The resulting suspension was then filtered. The filter cake was then recrystallized from methanol/diethyl ether to give 16.18 g (59% yield based on 1,2,3,4-tetrahydronaphthalene-1-one) of the desired product as a light tan solid; $^1$H NMR (CD$_3$OD) δ 2.31–2.40 (m, 2H), 2.80 (t, 2H, J=8 Hz), 4.0 (s, 2H), 6.26 (t, 1H, J=4.5 Hz), 7.19–7.29 (m, 4H).

EXAMPLE 9

8-Hydroxy-7-methoxy-1-(spiro-1'-1',2',3',4'-tetrahydronaphthalene)-2,3,4,5-tetrahydro-1H-3-benzazepine hydrochloride Step 1:
8-Hydroxy-7-methoxy-4-oxo-1-(spiro-1'-1',2',3',4'-tetrahydronaphthalene)-2,3,4,5-tetrahydro-1H-3-benzazepine Following the procedures described in Example 5, replacing 1-aminomethyl-1-hydroxyindan with 1-aminomethyl-1-hydroxy-1,2,3,4-tetrahydronaphthalene (the product of Example 7), the title compound was prepared; $^1$H NMR (CDCl$_3$) δ 1.70–1.96 (m, 2H), 1.98–2.10 (m, 1H), 2.20–2.30 (m, 1H), 2.80–3.05 (m, 2H), 3.49 (dd, 1H, J=15, 6 Hz), 3.65 (d, 1H, J=15 Hz), 3.78–3.89 (m, 1H), 3.86 (s, 3H), 4.14 (d, 1H, J=15 Hz), 5.40 (s, 1H), 6.43 (s, 1H), 6.57 (s, 1H), 6.75 (d, 1H, J=9 Hz), 6.96–7.13 (m, 3H).

Step 2:
8-Hydroxy-7-methoxy-1-(spiro-1'-1',2',3',4'-tetrahydronaphthalene)-2,3,4,5-tetrahydro-1H-3-benzazepine hydrochloride To a solution of 8-hydroxy-7-methoxy-4-oxo-1-(spiro-1'-1',2',3',4'-tetrahydronaphthalene)-2,3,4,5-tetrahydro-1H-3-benzazepine (1.18 g, 3.7 mmol), from Step 1, in 75 mL of THF was added, in portions, lithium aluminum hydride (LAH: 0.56 g, 15 mmol, 4 equivalents). The resulting suspensions was refluxed under nitrogen for 14 hours. THF (500 mL) was added and the unreacted LAH was quenched with excess sodium sulfate decahydrate. The solids were filtered over Celite ® filter aid and the filtrate was concentrated under reduced pressure to give a pale yellow glass. The glass was dissolved in methylene chloride (~5 mL) and ~1 mL of a 5M solution of hydrogen chloride in diethyl ether was added to precipitate the HCl salt of the product. The precipitate was recrystallized from methanol/methylene chloride/diethyl ether to give 0.45 g (35% yield) of the title compound; DCI MS M/Z: 310 (M+H)$^+$; IR (KBr): 3430, 2940, 1615, 1585, 1275, 760 cm$^{-1}$; $^1$H NMR (CD$_3$OD) δ 1.61–1.75 (m, 1H), 1.78–1.88 (m, 1H), 1.97–2.08 (m, 1H), 2.26–2.36 (m, 1H), 2.85–2.93 (m, 2H), 3.19–3.39 (m, 3H), 3.42 (d, 1H, J=13.5 Hz), 3.53–3.61 (m, 1H), 3.82 (s, 3H), 3.86 (d, 1H, J=13.5 Hz), 6.03 (s, 1H), 6.76 (s, 1H), 7.00 (d, 1H, J=7.5 Hz), 7.12–7.23 (m, 3H). Analysis calculated for C$_{20}$H$_{24}$ClNO$_2$: C, 69.45; H, 6.70; N, 4.05. Found: C, 69.05; H, 7.04; N, 4.00.

EXAMPLE 10

8-Hydroxy-7-methoxy-3-methyl-1-(spiro-1'-1',2',3',4'-tetrahydronaphthalene)-2,3,4,5-tetrahydro-1H-3-benzazepine hydrochloride To a suspension of 8-hydroxy-7-methoxy-1-(spiro-1'-1',2',3',4'-tetrahydronapthalene)-2,3,4,5-tetrahydro-1H-3-benzazepine (1.0 g, 3.2 mmol), the product of Example 9, in 20 mL of acetonitrile, was added 37% aqueous formaldehyde (1mL, 13 mmol, 4 equivalents), followed by sodium cyanoborohydride (0.57 g, 9.6 mmol, 3 equivalents). The resulting mixture was stirred at ambient temperature for 2.5 hours. Aqueous 1N hydrochloric acid solution (30 mL) was added and the acetonitrile was removed under reduced pressure. The aqueous mixture was made basic with ammonium hydroxide and then extracted with 2×100 mL of methylene chloride. The combined organic layers were washed with water, dried over anhydrous magnesium sulfate, filtered and concentrated under reduced pressure to give a pale yellow solid. The solid was purified by flash chromatography on silica gel eluting with ammonium hydroxide/ethyl acetate/methylene chloride (1:50:50) to give the free amine of the desired product. The free amine was dissolved in methylene chloride (~5 mL) and to the resultant solution was added ~1 mL of a 5M solution of hydrogen chloride in diethyl ether to precipitate the hydrochloride salt of the product. The precipitate was recrystallized from methanol/methylene chloride/diethyl ether to give 0.47 g (41% yield) of the title compound; DCI MS M/Z: 324 (M+H)$^+$; IR (KBr): 3430, 2940, 1615, 1515, 1460, 1275, 760 cm$^{-1}$; $^1$H NMR (CD$_3$OD) δ 1.53–1.75 (m, 1H), 1.79–1.91 (m, 1H), 1.99–2.09 (m, 1H), 2.30–2.41 (m, 1H), 2.85–2.93 (m, 3H), 3.02 (s, 3H), 3.21–3.42 (m, 2H), 3.49–3.55 (m, 1H), 3.70–3.77 (m, 1H), 3.83 (s, 3H), 4.00 (d, 1H, J=15 Hz), 5.99 (s, 1H), 6.77 (s, 1H), 7.02–7.06 (m, 1H), 7.15–7.25 (m, 3H). Analysis calculated for C$_{21}$H$_{26}$ClNO$_2$.0.8H$_2$O: C, 67.39; H, 7.43; N, 3.72. Found: C, 67.26; H, 7.53; N, 3.62.

EXAMPLE 11

8-Hydroxy-7-(methylthio)-3-methyl-1-(spiro-1'-1',2',3',4'-tetrahydronaphthalene)-2,3,4,5-tetrahydro-1H-3-benzazepine hydrochloride Step 1:
8-Hydroxy-7-methylthio-4-oxo-1-(spiro-1'-1',2',3',4'-tetrahydronaphthalene)-2,3,4,5-tetrahydro-1H-3-benzazepine Following the procedures described in Steps 1 and 2 of Example 5, replacing 4-benzyloxy-3-methoxyphenylacetyl chloride with 4-methoxy-3-methylthiophenylacetic acid, the product of Example 3, the title compound was prepared; $^1$H NMR (CDCl$_3$) δ 2.42 (m, 5H), 3.08 (m, 2H), 3.52 (m, 2H), 3.584 (s, 3H), 3.92 (m, 2H), 6.23 (br t, 1H, J=7.5 Hz), 6.30 (s, 1H), 6.78 (d, 1H, J=79.0 Hz), 6.87 (s, 1H), 7.09 (br t, 1H, J=7.0 Hz), 7.24 (m, 2H)

Step 2:
8-Hydroxy-7-(methylthio)-1-(spiro-1'-1',2',3',4'-tetrahydronaphthalene)-2,3,-dihydro-1H-3-benzazepine To a cold (−10° C.) solution of 8-hydroxy-7-methylthio-4-oxo-1-(spiro-1'-1',2',3',4'-tetrahydronaphthalene)-2,3,4,5-tetrahydro-1H-3-benzazepine (0.54 g, 16 mmol) from Step 1 in 15 mL of THF under nitrogen, was added 6.4 mL of a 1M solution of borane in THF (6.4 mmol, 4 equivalents). Cooling was discontinued and the reaction mixture was stirred at ambient temperature for 20 hours. The reaction mixture was then concentrated under reduced pressure and water (100 mL) was added. The resultant aqueous mixture was extracted with 2×100 mL of methylene chloride and the combined organic layers were washed with 100 mL of a 1M aqueous solution of sodium hydroxide, followed by 200 mL of 1:1 water/brine. The organic solution was dried over anhydrous magnesium sulfate, filtered and concentrated to give the title compound as a white solid. The title compound was used directly in the next step.

Step 3:
8-Hydroxy-3-methyl-7-(methylthio)-1-(spiro-1'-1',2',3',4'-tetrahydronaphthalene)-2,3,4,5-tetrahydro-1H-3-benzazepine hydrochloride To a turbid solution of 8-hydroxy-7-(methylthio)-1-(spiro-1'-1',2',3',4'-tetrahydronaphthalene)-2,3-dihydro-1H-3-benzazepine (0.25 g, 0.77 mmol), from Step 2, in 10 mL of acetonitrile was added 0.3 mL (3.9 mmol, 5 equivalents) of 37% aqueous formaldehyde. The resulting clear solution was stirred at ambient temperature for 10 minutes and then sodium cyanoborohydride (0.15 g, 2.3 mmol, 3 equivalents) was added. The resulting mixture was stirred for 3 hours and then 10 mL of 2N hydrochloric acid was added. The reaction mixture was then made basic with ammonium hydroxide and extracted with 2×50 mL of methylene chloride. The combined organic layers were dried over anhydrous magnesium sulfate, filtered and concentrated to give a white solid. The solid was dissolved in 5 mL of methylene chloride and hydrogen chloride (1 mL of a 5M solution in diethyl ether) was added to precipitate the hydrochloride salt. The precipitate was recrystallized from methanol/methylene chloride/diethyl ether to give 0.13 g (45% yield) of the title compound; DCI MS M/Z: 340 (M+H)+; IR (KBr): 3420, 3090, 2950, 2710, 1595, 1400, 1220, 760 cm$^{-1}$; $^1$H NMR (CD$_3$OD) δ 1.56–1.75 (m, 1H), 1.80–1.93 (m, 1H), 2.31–2.41 (m, 1H), 2.36 (s, 3H), 2.85–2.94 (m, 3H), 3.01 (s, 3H), 3.22–3.43 (m, 2H), 3.49–3.58 (m, 1H), 3.68–3.77 (m, 1H), 4.02 (d, 1H, J=13.5 Hz), 6.02 (s, 1H), 7.02–7.27 (m, 5H). Analysis calculated for $C_{21}H_{26}ClNOS$: C, 67.09; H, 6.97; N, 3.73. Found: C, 66.87; H, 7.00; N, 3.68.

EXAMPLE 12

8-Methoxy-4-oxo-1-(spiro-1'-indan)-2,3,4,5-tetrahydro-1H-3-benzazepine

To a stirred solution of 8-methoxy-4-oxo-7-methylthio-1-(spiro-1'-indan)-2,3,4,5-tetrahydro-1H-3-benzazepine (3.5 g, 13.4 mmol), prepared from 4-methoxy-3-methylthiophenylacetic acid (the product of Example 3) and 1-aminomethyl-1-hydroxyindan (the product of Example 1) by the procedures described in Step 1 of Example 11, in 250 mL of absolute ethanol was added 35 g of Raney nickel. The reaction mixture was refluxed for 3 hours and then cooled to ambient temperature and filtered through Celite ® filter aid. The filtrate was concentrated under reduced pressure to give a white powder which was triturated with methylene chloride and diethyl ether to give 2.8 g (97% yield) of the title compound as a white powder; $^1$H NMR (CDCl$_3$) δ 2.35 (m, 1H), 2.45 (m, 1H), 3.03 (m, 2H), 3.40 (dd, 1H, J=6.0, 12 Hz), 3.56 (dd, 1H, J=7.0, 12 Hz), 3.60 (s, 3H), 3.80 (d, 1H, J=15 Hz), 3.97 (d, 1H, J=15 Hz), 6.43 (s, 1H), 6.67 (m, 1H), 6.78 (d, 1H, J=6.5 Hz), 6.92 (br s, 1H), 7.04 (m, 1H), 7.16 (t, 1H, J=6.0 Hz), 7.25 (d, 1H, J=6.0 Hz).

EXAMPLE 13

8-Hydroxy-1-(spiro-1'-indan)-2,3,4,5-tetrahydro-1H-3-benzazepine hydrobromide

Step 1:
8-Methoxy-1-(spiro-1'-indan)-2,3,4,5-tetrahydro-1H-3-benzazepine

To a stirred solution of 8-methoxy-4-oxo-1-(spiro-1'-indan)-2,3,4,5-tetrahydro-1H-3-benzazepine (320 mg, 1.48 mmol), the product of Example 12, in 15 mL of anhydrous THF was added lithium aluminum hydride (112 mg, 2.97 mmol). The resulting mixture was refluxed for 18 hours and then cooled to ambient temperature and quenched with sodium sulfate decahydrate. The resultant slurry was filtered over Celite ® filter aid and the filtrate was concentrated to give 175 mg (60% yield) of the title compound as a pale yellow foam; $^1$H NMR (CDCl$_3$) δ 2.04 (br s, 1H), 2.43 (m, 2H), 2.83 (m, 4H), 3.08 (d, 1H, J=15 Hz), 3.28 (m, 2H), 3.43 (d, 1H, J=15 Hz), 3.53 (s, 3H), 6.02 (d, 1H, J=4 Hz), 6.54 (dd, 1H, J=4, 9 Hz), 7.02 (d, 1H, J=10 Hz), 7.17 (m, 1H), 7.25 (m, 3H).

Step 2:
8-Hydroxy-1-(spiro-1'-indan)-2,3,4,5-tetrahydro-1H-3-benzazepine hydrobromide To a stirred solution of 8-methoxy-1-(spiro-1'-indan)-2,3-dihydro-1H-3-benzazepine (80 mg, 0.40 mmol), from Step 1, in 4 mL of anhydrous methylene chloride cooled to −78° C., was added a 1M solution of boron tribromide in methylene chloride (0.796 mL, 0.796 mmol, 2 equivalents). The resulting solution was stirred at −78° C. for 2.5 hours and then allowed to warm to 0° C. and stirred for an additional 3 hours. The pale yellow solution was then cooled to −78° C. and the reaction was quenched with excess anhydrous methanol. The solution was concentrated under reduced pressure and the residue was triturated with methylene chloride/ethanol (10:1) and dried to give 80 mg (58% yield) of the title compound as a white powder, m.p. 255° C.; DCI MS M/Z: 266 (M+H)+; IR (KBr): 3400, 2960, 1580, 760 cm$^{-1}$; $^1$H NMR (CD$_3$OD) δ 2.43 (m, 2H), 2.84 (m, 1H), 2.97 (m, 1H), 3.14 (m, 2H), 3.40 (m, 1H), 3.50 (d, 1H, J=15 Hz), 3.60 (m, 1H), 3.78 (d, 1H, J=13 Hz), 5.87 (d, 1H, J=3 Hz), 6.56 (dd, 1H, J=3, 9 Hz), 7.05 (d, 1H, J=10 Hz), 7.20 (m, 1H), 7.33 (m, 3H). Analysis calculated for $C_{18}H_{20}BrNO.1.0C_2H_6O$: C, 61.23; H, 6.68; N, 3.57. Found: C, 60.88; H, 6.57; N, 3.55.

EXAMPLE 14

8-Hydroxy-3-methyl-1-(spiro-1'-indan)-2,3,4,5-tetrahydro-1H-3-benzazepine hydrobromide Step 1:
8-Methoxy-1-(spiro-1'-indan)-2,3-dihydro-1H-3-benzazepine To a stirred solution of 8-methoxy-4-oxo-1-(spiro-1'-indan)-2,3,4,5-tetrahydro-1H-3-benzazepine (3.0 g, 13.93 mmol), the product of Example 12, in 120 mL of anhydrous THF at ambient temperature, was added 42 mL of a 1M solution of borane in THF (42 mmol, 3 equivalents). After the initial foaming subsided, the reaction mixture was stirred at ambient temperature for 3 hours and then the reaction was quenched with water (50 mL). The reaction mixture was extracted with 2×150 mL of methylene chloride. The combined organics were washed with 2×50 mL of 50% aqueous ammonium hydroxide solution, 2×50 mL of water and 50 mL of brine, dried over anhydrous magnesium sulfate, filtered and concentrated under reduced pressure to give the title compound as a foam. The product of Step 1 was carried on to the next step without purification.

Step 2: 8-Methoxy-1-(spiro-1'-indan)-3-benzazepine

To a stirred solution of 8-methoxy-1-(spiro-1'-indan)-2,3-dihydro-1H-3-benzazepine (2.5 g, 11.6 mmol), from Step 1, in 100 mL of glacial acetic acid, was added in one portion, sodium cyanoborohydride (1.46 g, 23.4 mmol, 2 equivalents). After the initial foaming subsided, the reaction mixture was stirred at ambient temperature for 18 hours. The acetic acid was removed under reduced pressure and the residue dissolved in 150 mL of methylene chloride. The methylene chloride solution was washed with 2×50 mL of saturated aqueous sodium bicarbonate, 2×50 mL of water and 50 mL of brine, dried over anhydrous magnesium sulfate, filtered and concentrated to a viscous oil (2.2 g). The oil was chromatographed on silica gel eluting with methylene chloride/methanol/ammonium hydroxide (89:9:1) to give 1.7 g (68% yield) of the title compound as a white foam; $^1$H NMR (CDCl$_3$) δ 2.06 (br s, 1H), 2.43 (m, 2H), 2.82 (m, 4H), 3.09 (d, 1H, J=13 Hz), 3.30 (m, 2H), 3.43 (d, 1H, J=12.5 Hz), 3.58 (s, 3H), 6.03 (d, 1H, J=3.0 Hz), 6.57 (dd, 1H, J=3.0, 9.0 Hz), 7.03 (d, 1H, J=10 Hz), 7.24 (m, 4H).

Step 3:
8-Methoxy-3-methyl-1-(spiro-1'-indan)-2,3,4,5-tetrahydro-1H-3-benzazepine To a stirred solution of 8-methoxy-1-(spiro-1'-indan)-2,3,4,5-tetrahydro-1H-3-benzazepine (120 mg, 0.56 mmol) in 6 mL of anhydrous acetonitrile was added 57% aqueous formaldehyde (0.23 mL, 2.8 mmol, 5 equivalents) followed by sodium cyanoborohydride (105 mg, 1.68 mmol, 5 equivalents). After the initial foaming subsided, the reaction mixture was stirred at ambient temperature for 3 h and then concentrated under reduced pressure. The residue was dissolved in 100 mL of methylene chloride. The methylene chloride solution was washed with 3×25 mL of 50% aqueous ammonium hydroxide solution, 2×50 mL of water and 50 mL of brine, dried over anhydrous magnesium sulfate, filtered and concentrated under reduced pressure to give 110 mg (94% yield) of the title compound as a white foam. The product of Step 3 was carried on in the synthesis without purification.

Step 4:
8-Hydroxy-3-methyl-1-(spiro-1'-indan)-2,3,4,5-tetrahydro-1H-3-benzazepine hydrobromide To a stirred solution of 8-methoxy-3-methyl-1-(spiro-1'-indan)-2,3,4,5-tetrahydro-1H-3-benzazepine (295 mg, 1.36 mmol), from Step 3, in 15 mL of methylene chloride cooled to −78° C., was added 2.75 mL of a 1M solution of boron tribromide in methylene chloride (2.75 mmol BBr$_3$, 2 equivalents). The resulting solution was allowed to warm to ambient temperature. The solution was stirred at ambient temperature for 4 hours and then cooled to −78° C. The reaction was quenched with excess anhydrous methanol and the reaction mixture was concentrated under reduced pressure. The residue was crystallized from methylene chloride/diethyl ether to give 150 mg (30% yield) of the title compound as a white powder, m.p. 272°–274° C.; IR (KBr): 3300, 3240, 1630, 1460, 760 cm$^{-1}$; $^1$H NMR (CD$_3$OD) δ 2.4 (m, 1H), 2.55 (m, 1H), 2.85 (m, 1H), 2.93 (m, 1H), 3.02 (s, 3H), 3.20 (m, 2H), 3.42 (m, 1H), 3.53 (d, 1H, J=14 Hz), 3.74 (m, 1H), 3.91 (d, 1H, J=15 Hz), 5.85 (d, 1H, J=3 Hz), 6.57 (dd, 1H, J=3, 10 Hz), 7.05 (d, 1H, J=8.5 Hz), 7.21 (m, 1H), 7.35 (m, 3H). Analysis calculated for C$_{19}$H$_{22}$BrNO.1.0HBr: C, 61.49; H, 6.05; N, 3.80. Found: C, 61.71; H, 6.01; N, 3.98.

EXAMPLE 15

7,8-Dihydroxy-1-(spiro-1'-indan)-2,3,4,5-tetrahydro-1H-3-benzazepine hydrobromide Step 1:
7,8-Dimethoxy-1-(spiro-1'-indan)-2,3-dihydro-1H-3-benzazepine To a stirred solution of 7,8-dimethoxy-4-oxo-1-(spiro-1'-indan)-2,3,4,5-tetrahydro-1H-3-benzazepine (3.2 g, 13 mmol), the product of Example 6, in 130 mL of anhydrous THF, at ambient temperature, was added 40 mL of a 1M solution of borane THF complex in THF (39.1 mmol BH$_3$, 3 equivalents). After the initial foaming subsided, the clear solution was stirred at ambient temperature for 3 hours. The reaction was then quenched with water (50 mL) and then extracted with 2×150 mL of methylene chloride. The combined organic layers were washed with 2×50 mL of saturated aqueous sodium bicarbonate solution, 50 mL of water and 50 mL of brine, dried over anhydrous magnesium sulfate, filtered and concentrated under reduced pressure to give 2.5 g (85% yield) of the title compound; $^1$H NMR (CDCl$_3$) δ 1.40 (m, 1H), 1.55 (m, 1H), 2.35 (m, 2H), 2.91 (m, 2H), 3.32 (m, 1H), 3.42 (s, 3H), 3.85 (s, 3H), 4.30 (br s, 1H), 5.87 (s, 1H), 6.53 (s, 1H), 7.13 (m, 1H), 7.30 (m, 3H).

Step 2:
7,8-Dimethoxy-1-(spiro-1'-indan)-2,3,4,5-tetrahydro-1H-3-benzazepine

To a stirred solution of 7,8-dimethoxy-1-(spiro-1'-indan)-2,3,4,5-tetrahydro-1H-3-benzazepine-4-one (1.0 g, 3.09 mmol), from Step 1, in 20 mL of anhydrous THF, was added in one portion lithium aluminum hydride (0.235 mg, 6.18 mmol, 2 equivalents). The resulting mixture was refluxed for 18 hours, cooled to ambient temperature and the reaction was quenched with excess sodium sulfate decahydrate. The reaction mixture was filtered over Celite® filter aid and the filtrate was concentrated to a viscous oil. The oil was chromatographed on silica gel eluting with methylene chloride/methanol/ammonium hydroxide (89:9:1) to give 425 mg (44% yield) of the title compound as a light amber oil; $^1$H NMR (CDCl$_3$) δ 2.13 (br s, 1H), 2.40 (m, 2H), 2.83 (m, 4H), 3.07 (d, 1H, J=10 Hz), 3.30 (m, 2H), 3.38 (s, 0.5H), 3.43 (s, 3.5H), 3.73 (s, 3H), 5.97 (s, 1H), 6.63 (s, 1H), 7.15 (m, 1H), 7.26 (m, 3H).

Step 3: 7,8-Dihydroxy-1-(spiro-1'-indan)-3-benzazepine hydrobromide

To a stirred solution of 7,8-dimethoxy-4-oxo-1-(spiro-1'-indan)-2,3,4,5-tetrahydro-1H-3-benzazepine (340 mg, 1.1 mmol), from Step 2, in 11 mL of anhydrous methylene chloride cooled to −78° C., was added 3.30 mL of a 1M solution of boron tribromide in methylene chloride (3.30 mmol BBr$_3$, 3 equivalents). The resulting light orange-colored solution was allowed to warm to 0° C. over a period of 2 hours and then it was cooled to −78° C. The reaction was quenched with 60 mL of anhydrous methanol and the reaction mixture was allowed to warm to ambient temperature. The light yellow-colored solution was concentrated under reduced pressure and chased with 50 mL of anhydrous methanol. The resulting residue was triturated with diethyl ether and methylene chloride and dried to give 200 mg (50% yield) of the title compound as a white powder, m.p. 288°–290° C.; DCI MS M/Z: 282 (M+H)+; IR (KBr): 3300, 3200, 1600, 1510, 760 cm$^{-1}$; $^1$H NMR (CD$_3$OD) δ 2.41 (m, 2H), 2.93 (m, 4H), 3.17 (m, 1H), 3.43 (d, 1H, J=10 Hz), 3.73 (d, 1H), J=10 Hz), 5.87 (s, 1H), 6.6 (s, 1H), 7.17 (m, 1H), 7.32 (m, 3H). Analysis calculated for C$_{18}$H$_{20}$BrNO.0.5CH$_2$Cl$_2$: C, 54.90; H, 5.23; N, 3.46. Found: C, 55.11; H, 5.38; N, 3.40.

EXAMPLE 16

7,8-Dihydroxy-3-methyl-1-(spiro-1'-indan)-2,3,4,5-tetrahydro-1H-3-benzazepine formate Step 1:
7,8-Dimethoxy-3-methyl-1-(spiro-1'-indan)-2,3,4,5-tetrahydro-1H-3-benzazepine To a solution of 7,8-dimethoxy-1-(spiro-1'-indan)-2,3,4,5-tetrahydro-1H-3-benzazepine (0.77 g, 2.5 mmol) in 25 mL of acetonitrile was added 0.6 mL of 37% aqueous formaldehyde (7.5 mmol, 3 equivalents), followed by sodium cyanoborohydride (0.49 g, 7.6 mmol, 3.1 equivalents). The resulting mixture was stirred at ambient temperature for 4.5 hours and then the acetonitrile was removed under reduced pressure. The reaction was quenched with 1M aqueous hydrochloric acid solution (25 mL) and the resulting aqueous solution was made basic with 3M aqueous sodium hydroxide solution and extracted with 2×75 mL of diethyl ether. The combined organic layers were dried over anhydrous magnesium sulfate, filtered and concentrated under reduced pressure to a tan oil. The oil was purified by flash chromatography on silica gel eluting with ammonium hydroxide/ethyl acetate/methylene chloride (1:40:60) to give 0.49 g (60% yield) of the title compound as a white solid; $^1$H NMR (CDCl$_3$) δ 2.24–2.36 (m, 2H), 2.39 (s, 3H), 2.51–2.66 (m, 1H), 2.71–2.92 (m, 5H), 3.04–3.12 (m, 1H), 3.31–3.42 (m, 1H), 3.45 (s, 3H), 3.85 (s, 3H), 5.95 (s, 1H), 6.63 (s, 1H), 7.18–7.36 (m, 4H).

Step 2:
7,8-Dihydroxy-3-methyl-1-(spiro-1'-indan)-2,3,4,5-tetrahydro-1H-3-benzazepine formate To a solution of 7,8-dimethoxy-3-methyl-1-(spiro-1'-indan)-2,3,4,5-tetrahydro-1H-3-benzazepine (0.49 g, 1.5 mmol) in 15 mL of methylene chloride at −78° C., under nitrogen, was added 4.5 mL of a 1M solution of boron tribromide in methylene chloride (4.5 mmol BBr$_3$, 3 equivalents). The reaction mixture was stirred at −78° C. for 1 hour and then at ambient temperature for 4 hours. The reaction mixture was then cooled to −78° C. and the reaction was quenched with cold (−78° C.) methanol. The resulting solution was concentrated under reduced pressure and chased with methanol (2×50 mL) to give a brown oil. The oil was purified by flash chromatography on silica gel eluting with 85% formic acid/water/ethyl acetate (1:1:18) to give 120 mg (23% yield) of the title compound compound, m.p. 145°–155° C.; DCI MS M/Z: 296 (M+H)+; IR (KBr): 3420, 1600, 1510, 1455, 1350, 760 cm$^{-1}$; $^1$H NMR (CD$_3$OD) δ 2.32–2.53 (m, 2H), 2.76–3.08 (m, 3H), 2.44(s,3H), 3.10–3.20 (m, 1H), 3.32–3.44 (m, 1H), 3.53–3.69 (m, 2H), 3.76 (d, 1H), 5.84 (s, 1H), 6.65 (s, 1H), 7.17–7.23 (m, 1H), 7.30–7.39 (m, 3H).

EXAMPLE 17

7-Bromo-8-hydroxy-1-(spiro-1'-indan)-2,3,4,5-tetrahydro-1H-2,3,4,5-tetrahydro-1H-3-benzazepine hydrochloride To a stirred solution of 8-hydroxy-1-(spiro-1'-indan)-2,3,4,5-tetrahydro-1H-3-benzazepine hydrobromide (250 mg, 0.942 mmol), the product of Example 13, in 5 mL of formic acid cooled to 0° C. was added, in one portion via syringe, 48 μL (0.942 mmol, 1 equivalent) of bromine. The resulting pale yellow solution was stirred for 0.5 hour and then made basic with 50% aqueous ammonium hydroxide. The resulting mixture was extracted with 3×25 mL of methylene chloride. The combined organic layers were washed with 3×25 mL of water and 25 mL of brine, dried over anhydrous magnesium sulfate, filtered and concentrated in vacuo to a pale yellow foam. The foam (200 mg) was dissolved in a minimum amount of methylene chloride and the methylene chloride solution was diluted with diethyl ether. To the resulting solution at ambient temperature was added several drops of a 5M solution of hydrogen chloride in diethyl ether. The resulting white precipitate was filtered and dried to give 185 mg, (52% yield) of the title compound as a white powder, m.p. >285° C.; DCI MS M/Z: 344 (M+H)+, 346 (M+3)+; IR (KBr): 3300, 2910, 1600, 1400, 760 cm$^{-1}$; $^1$H NMR (CD$_3$OD)δ 2.43 (m, 2H), 2.85 (m, 1H), 2.97 (m, 1H), 3.17 (m, 2H), 3.33 (m, 1H), 3.50 (d, 1H, J=13 Hz), 3.60 (m, 1H), 3.80 (d, 1H, J=14 Hz), 6.03 (s, 1H), 7.22 (m, 1H), 7.37 (m, 4H). Analysis calculated for C$_{18}$H$_{19}$BrClNO.0.5HCl: C, 55.26; H, 5.25; N, 3.39. Found: C, 55.08; H, 5.06; N, 3.29.

EXAMPLE 18

7-Bromo-8-hydroxy-3-methyl-1-(spiro-1'-indan)-2,3,4,5-tetrahydro-1H-3-benzazepine hydrochloride To a stirred solution of 8-hydroxy-1(spiro-1'-indan)-3-methyl-2,3,4,5-tetrahydro-1H-3-benzazepine hydrobromide (250 mg, 0.69 mmol), the product of Example 14, in 12 mL of formic acid cooled to 0° C., was added, in one portion via syringe, 35 μL (0.69 mmol, 1 equivalent) of bromine. The resulting solution was stirred for 30 minutes and then it was made basic with 50% aqueous ammonium hydroxide solution. The mixture was then extracted with 3×25 mL of methylene chloride. The combined organic layers were washed with 3×20, mL of water and 20 mL of brine, dried over anhydrous magnesium sulfate, filtered and concentrated under reduced pressure to a foam. The foam (150 mg) was dissolved in diethyl ether to which was added several drops of a 5M solution of hydrogen chloride in diethyl ether. The resulting precipitate was collected and dried to give 155 mg (56% yield) of the title compound as a white powder, m.p. 232°–234° C.; DCI MS M/Z: 358 (M+H)+, 360 (M+3)+; IR ((KBr): 3400, 3100, 2680, 1600, 1400, 750 cm$^{-1}$; $^1$H NMR (CD$_3$OD) δ 2.80 (m, 1H), 2.93 (m, 1H), 3.23 (m, 1H), 3.36 (m, 1H), 3.38 (s, 3H), 3.50 (m, 1H), 3.63 (m, 1H), 3.84 (m, 1H), 4.03 (d, 1H, J=10 Hz), 4.12 (m, 1H), 4.30 (d, 1H, J=10 Hz), 6.38 (s, 1H), 7.6 (m, 1H), 7.75 (m, 4H). Analysis calculated for C$_{19}$H$_{21}$BrClNO.0.5HCl: C, 56.26; H, 5.55; N, 3.29. Found: C, 55.88; H, 5.46; N, 3.24.

EXAMPLE 19

8-Hydroxy-7-nitro-1-(spiro-1'-indan)-2,3,4,5-tetrahydro-1H-3-benzazepine hydrochloride To a stirred solution of 8-hydroxy-1(spiro-1'-indan)-2,3,4,5-tetrahydro-1H-3-benzazepine hydrobromide (400 mg, 1.15 mmol), the product of Example 13, in 15 mL of glacial acetic acid is added 0.5 mL of fuming nitric acid. The reaction mixture is stirred at ambient temperature for 1 hour and then it is concentrated in vacuo. The residue is dissolved in 100 mL of methylene chloride and the resultant solution is washed with $2\times 30$ mL of 50% aqueous ammonium hydroxide solution, $3\times 30$ mL of water and 30 mL of brine, dried over anhydrous magnesium sulfate, filtered and concentrated under reduced pressure to afford the desired product as the free amine. The amine is then taken up in diethyl ether to which is added several drops of a 5M solution of hydrogen chloride in diethyl ether. The precipitate is filtered and dried to give the title compound.

EXAMPLE 20

7-Amino-8-hydroxy-1-(spiro-1'-indan)-2,3,4,5-tetrahydro-1H-3-benzazepine dihydrochloride To a stirred solution of 8-hydroxy-7-nitro-1-(spiro-1'-indan)-2,3,4,5-tetrahydro-1H-3-benzazepine hydrochloride (500 mg, 1.45 mmol), the product of Example 19, in 15 mL of anhydrous THF cooled to 0° C. is added lithium aluminum hydride (110 mg, 2.90 mmol, 3 equivalents). The reaction mixture is stirred at ambient temperature for 2 hours and then the reaction is quenched with sodium sulfate decahydrate. The reaction mixture is filtered and concentrated under reduced pressure. The residue is dissolved in diethyl ether and several drops of a 5M solution of hydrogen chloride in diethyl ether is added. The precipitate is filtered and dried to afford the title compound.

EXAMPLE 21

8-Hydroxy-7-nitro-3-methyl-1-(spiro-1'-indan)-2,3,4,5-tetrahydro-1H-3-benzazepine hydrochloride To a stirred solution of 8-hydroxy-3-methyl-1(spiro-1'-indan)-2,3,4,5-tetrahydro-1H-3-benzazepine hydrobromide (400 mg, 1.21 mmol), the product of Example 14, in 15 mL of glacial acetic acid cooled to 20° C., was added 0.5 mL of fuming nitric acid. The reaction solution was stirred for 1 hour and then concentrated under reduced pressure. The residue was dissolved in 100 mL of methylene chloride and the resultant solution was washed with 25 mL of saturated aqueous sodium bicarbonate, 25 mL of water and 25 mL of brine, dried over anhydrous magnesium sulfate, filtered and concentrated to a foam. The foam was dissolved in a minimum amount of methylene chloride and the solution was diluted with diethyl ether. To the resulting pale yellow solution was added several drops of a 5M solution of hydrogen chloride in diethyl ether. The precipitate was filtered and dried to give 150 mg (37% yield) of the title compound, m.p. 262°–263° C.; DCI MS M/Z: 323 (M+H)+, 263 (M+NH₄)+; IR (KBr): 3440, 2950, 1630, 1580, 1520, 1420, 1300, 1220, 760 cm⁻¹; ¹H NMR (CD₃OD) δ 1.57 (m, 1H), 1.90 (m, 1H), 2.15 (m, 1H), 2.40 (m, 1H), 2.92 (m, 2H), 3.03 (s, 3H), 3.45 (m, 1H), 3.62 (d, 1H, J=11 Hz), 3.75 (m, 1H), 4.12 (d, 1H, J=10 Hz), 6.27 (s, 1H), 7.08 (m, 1H), 7.28 (m, 3H), 7.98 (s, 1H). Analysis calculated for C₁₉H₂₁ClN₂O₃.0.3HCl.0.3Et₂O: C, 61.58; H, 6.22; N, 7.11. Found: C, 61.48; H, 6.09; N, 7.06.

EXAMPLE 22

7-Amino-8-hydroxy-3-methyl-1-(spiro-1'-indan)-2,3,4,5-tetrahydro-1H-3-benzazepine dihydrochloride To a stirred solution of 8-hydroxy-7-nitro-1(spiro-1'-indan)-2,3,4,5-tetrahydro-1H-3-benzazepine hydrobromide (400 mg, 1.21 mmol), the product of Example 21, in 15 mL of anhydrous THF cooled to 0° C. is added lithium aluminum hydride (105 mg, 2.78 mmol, 2 equivalents). The reaction mixture is stirred at ambient temperature for 2 hours and then it is poured into an Erlenmeyer flask and diluted with 50 mL of anhydrous THF. The reaction is quenched with excess sodium sulfate decahydrate and the resulting slurry is filtered over Celite ® filter aid. The filtrate is concentrated under reduced pressure to give the desired product as the free amine. The amine is dissolved in diethyl ether and several drops of a 5M solution of hydrogen chloride in diethyl ether is added. The precipitate is filtered and dried to afford the title compound.

EXAMPLE 23

7-Acetylamino-8-hydroxy-3-methyl-1-(spiro-1'-indan)-2,3,4,5-tetrahydro-1H-3-benzazepine hydrochloride To a stirred solution of 7-amino-8-hydroxy-3-methyl-1-(spiro-1'-indan)-2,3,4,5-tetrahydro-1H-3-benzazepine dihydrochloride (500 mg, 1.36 mmol), the product of Example 22, in 7 mL of methylene chloride is added 7 mL of saturated aqueous sodium bicarbonate solution, followed by acetyl chloride (100 μL, 1.36 mmol) via syringe. The mixture is stirred vigorously for 2 hours and then methylene chloride is added and the layers are separated. The organic layer is washed with 25 mL of water, $2\times 25$ mL of 50% aqueous ammonium hydroxide and 25 mL of brine, dried over anhydrous magnesium sulfate, filtered and concentrated under reduced pressure to give the desired product as the free amine. The amine is dissolved in diethyl ether and several drops of a 5M solution of hydrogen chloride in diethyl ether is added. The precipitate is filtered and dried to afford the title compound.

EXAMPLE 24

8-Hydroxy-7-methoxy-1-(spiro-1'-indan)-2,3,4,5-tetrahydro-1H-3-benzazepine hydrochloride Following the procedures described in Step 2 of Example 9, replacing 8-hydroxy-7-methoxy-4-oxo-1-(spiro-1'-1',2', 3',4'-tetrahydronaphthalene)-2,3,4,5-tetrahydro-1H-3-benzazepine with 8-hydroxy-7-methoxy-4-oxo-1-(spiro-1'-indan)-2,3,4,5-tetrahydro-1H-3-benzazepine, the product of Example 5, the title compound was prepared, m.p. 260° C; DCI MS M/Z: 296 (M+H)+; IR (KBr): 3420, 2920, 1620, 1600, 1550, 1500, 1200, 870, 810, 750 cm⁻¹; ¹H NMR (CD₃OD) δ 2.38–2.47 (m, 2H), 2.77–2.9 (m, 1H), 2.91–3.02 (m, 1H), 3.08–3.25 (m, 2H), 3.35–3.50(m, 2H), 3.56–3.65 (m, 1H), 3.75 (d, 1H, J=15 Hz), 3.82 (s, 3H), 5.89 (s, 1H), 6.82 (s, 1H), 7.14–7.21 (m, 1H), 7.30–7.40 (m, 3H). Analysis calculated for C₁₉H₂₂ClNO₂.0.3 H₂O: C, 67.67; H, 6.75: N, 4.13. Found: C, 67.51; H, 6.79; N, 4.01.

EXAMPLE 25

8-Hydroxy-7-methoxy-3-methyl-1-(spiro-1'-indan)-2,3,4,5-tetrahydro-1H-3-benzazepine hydrochloride Following the procedures described in Example 10, replacing 8-hydroxy-7-methoxy-1-(spiro-1'-1', 2', 3', 4'-tetrahydronapthalene)-2,3,4,5-tetrahydro-1H-3-benzazepine with 8-hydroxy-7-methoxy-1(spiro-1'-indan)-2,3,4,5-tetrahydro-1H-3-benzazepine hydrochoride, the product of Example 24, the title compound was prepared, m.p. 165°-167° C; DCI MS M/Z: 310 (M+H)+; IR (KBr): 3420, 2940, 2680, 1620, 1590, 1515, 1460, 1280, 1210, 760 cm$^{-1}$; $^1$H NMR (CD$_3$OD) δ 2.34–2.45 (m, 1H), 2.45–2.58 (m, 1H), 2.76–2.89 (m, 1H), 2.92–3.04 (m, 1H), 3.00 (s, 3H), 3.10–3.29 (m, 1H), 3.38–3.50 (m, 1H), 3.61 (d, 1H, J=14 Hz), 3.69–3.79 (m, 1H), 3.82 (s, 3H), 3.86 (d, 1H, J=14 Hz), 5.85 (s, 1H), 6.82 (s, 1H), 7.16–7.23 (m, 1H), 7.30–7.41 (m, 3H). Analysis calculated for C$_{20}$H$_{24}$ClNO$_2$.0.6 H$_2$O: C, 67.35; H, 7.12; N, 3.93. Found: C, 67.36; H, 7.18; N, 3.88.

EXAMPLE 26

7.8-Dihydroxy-1-(spiro-1'-1',2', 3',4'-tetrahydronapthalene)-2,3,4,5-tetrahydro-1H-3-benzazepine hydrobromide Following the procedures described in Example 15, replacing 7,8-dimethoxy-4-oxo-1-(spiro-1'-indan)-2,3,4,5-tetrahydro-1H-3-benzazepine with 7,8-dimethoxy-4-oxo-1-(spiro-1'-1',2',3', 4'-tetrahydronapthalene)-2,3,4,5-tetrahydro-1H-3-benzazepine (prepared from 3,4-dimethoxy-phenylacetyl chloride and 1-aminomethyl-1-3,4-dihydronaphthalene, the product of Example 8, according to the procedures described in Example 6), the title compound was prepared, m.p. 185°-189° C.; DCI MS M/Z: 296 (M+H)+; IR (KBr): 3300, 2950, 1610, 1550, 1425, 1280, 880, 760 cm$^{-1}$; $^1$H NMR (CD$_3$OD) δ 1.59–1.74 (m, 1H), 1.74–1.87 (m, 1H), 1.92–2.04 (m, 1H), 2.23–2.34 (m, 1H), 2.82–2.90 (m, 2H), 3.05–3.17 (m, 1H), 3.20–3.34 (m, 2H), 3.39 (d, 1H, J=15 Hz), 3.47–3.6 (m, 1H), 3.83 (d, 1H, J=15 Hz), 6.00 (s, 1H), 6.60 (s, 1H), 6.99–7.04 (m, 1H), 7.11–7.21 (m, 3H). Analysis calculated for C$_{19}$H$_{22}$BrNO$_2$.1.0 H$_2$O: C, 57.88; H, 6.14; N, 3.55. Found: C, 57.78; H, 6.28; N, 3.33.

EXAMPLE 27

7,8-Dihydroxy-3-methyl-1-(spiro-1'-1',2',3',4'-tetrahydronapthalene)-2,3,4,5-tetrahydro-1H-3-benzazepine hydrobromide Following the procedures described in Example 16, replacing 7,8-dihydroxy-3-methyl-1-(spiro-1'-indan)-2,3,4,5-tetrahydro-1H-3-benzazepine formate with 7,8-dihydroxy-3-methyl-1-(spiro-1'-1',2',3',4'-tetrahydronapthalene)-2,3,4,5-tetrahydro-1H-3-benzazepine hydrochloride, the product of Example 26, the title compound is prepared, m.p. 195°-200° C.; DCI MS M/Z: 310 (M+H)+; IR (KBr): 3420, 3250, 2940, 2690, 1620, 1515, 1450, 1270, 760 cm$^{-1}$; $^1$H NMR (CD$_3$OD) δ 1.52–1.73 (m, 1H), 1.76–1.89 (m, 1H), 1.95–2.06 (m, 1H), 2.27–2.38 (m, 1H), 2.81–2.92 (m, 2H), 2.99 (s, 3H), 3.07–3.19 (m, 1H), 3.35 (s, 1H), 3.42–3.52 (m, 2H), 3.62–3.75 (m, 1H), 3.98 (d, 1H, J=14 Hz), 5.96 (s, ⅔H), 6.00 (s, ⅓H), 6.60 (s, ⅔H), 6.69 (s, ⅓H), 7.02–7.10 (m, 1H), 7.13–7.23 (m, 3H). Analysis calculated for C$_{20}$H$_{24}$BrNO$_2$.0.3CH$_3$OH.0.4Et$_2$O: C, 61.23; H, 6.85; N, 3.26. Found: C, 61.13; H, 6.84; N, 3.30.

EXAMPLE 28

8-Hydroxy-1-(spiro-1'-1',2',3',4'-tetrahydronapthalene)-2,3,4,5-tetrahydro-1H-3-benzazepine hydrochloride Following the procedures described in Examples 12 and 13, starting with 8-hydroxy-7-methylthio-4-oxo-1-(spiro-1'-1',2',3',4'-tetrahydronaphthalene)-2,3,4,5-tetrahydro-1H-3-benzazepine, the product of Example 11, the title compound was prepared, m.p. 273°–275° C.; DCI MS M/Z: 280 (M+H)+; IR (KBr): 3410, 2950, 1600, 1400, 760 cm$^{-1}$; $^1$H NMR (CD$_3$OD) δ 1.67 (m, 1H), 1.83 (m, 1H), 2.05 (m, 1H), 2.33 (m, 1H), 2.90 (m, 2H), 3.20–3.60 (m, 4H), 3.90 (d, 1H, J=15 Hz), 6.04 (d, 1H, J=3.0 Hz) 6.57 (dd, 1H, J=12.0, 3.0 Hz), 7.02 (m, 2H), 7.25 (m, 3H). Analysis calculated for C$_{19}$H$_{22}$ClNO.0.2HCl: C, 70.62; H, 6.92; N, 4.34. Found: C, 70.81; H, 6.94; N, 4.37.

EXAMPLE 29

8-Hydroxy-3-methyl-1-(spiro-1'-1',2',3',4'-tetrahydronapthalene)-2,3,4,5-tetrahydro-1H-3-benzazepine hydrochloride Following the procedures described in Example 14, starting with 8-hydroxy-1-(spiro-1'-1',2',3',4'-tetrahydronapthalene)-2,3,4,5-tetrahydro-1H-3-benzazepine, the product of Example 28, the title compound was prepared, m.p. 255°-257° C.; DCI MS M/Z: 294 (M+H)+; IR (KBr): 3440, 1620, 1460, 760 cm$^{-1}$; $^1$H NMR (CD$_3$OD) δ 1.60 (m, 1H), 1.85 (m, 1H), 2.08 (m, 1H), 2.40 (m, 1H), 2.90 (m, 2H), 3.03 (s, 3H), 3.20–3.40 (m, 3H), 3.52 (d, 1H, J=13 Hz), 3.73 (m, 1H), 4.03 (d, 1H, J=13 Hz), 6.00 (d, 1H, J=3.0 Hz), 6.57 (dd, 1H, J=9.0, 3.0 Hz), 7.03 (m, 2H), 7.20 (m, 3H). Analysis calculated for C$_{20}$H$_{24}$ClNO: C, 72.82; H, 7.33; N, 4.25. Found: C, 72.59; H, 7.39; N, 4.26.

EXAMPLE 30

7-Bromo-8-hydroxy-1-(spiro-1'-1',2',3',4'-tetrahydronapthalene)-2,3,4,5-tetrahydro-1H-3-benzazepine hydrochloride Following the procedures described in Example 17, starting with 8-hydroxy-1-(spiro-1'-1',2',3',4'-tetrahydronapthalene)-2,3,4,5-tetrahydro-1H-3-benzazepine hydrochloride, the product of Example 28, the title compound was prepared, m.p. >275° C.; DCI MS M/Z: 358 (M+H)+; IR (KBr): 3420, 2950, 2680, 1600, 1480, 760 cm$^{-1}$; $^1$H NMR (CD$_3$OD) δ 1.63 (m, 1H), 1.85 (m, 1H), 2.05 (m, 1H), 2.30 (m, 1H), 2.87 (m, 2H), 3.20–3.60 (m, 4H), 3.90 (d, 1H, J=15 Hz), 6.17 (s, 1H), 7.02 (m, 2H), 7.05–7.25 (m, 4H), 7.35 (s, 1H). Analysis calculated for C$_{19}$H$_{21}$BrClNO.0.5HCl: C, 55.26; H, 5.25; N, 3.39. Found: C, 55.08; H, 5.06; N, 3.29.

EXAMPLE 31

7-Bromo-8-hydroxy-3-methyl-1-(spiro-1'-1',2',3',4'-tetrahydronapthalene)-2,3,4,5-tetrahydro-1H-3-benzazepine hydrochloride Following the procedures described in Example 18, starting with 8-hydroxy-3-methyl-1-(spiro-1'-1',2',3',4'-tetrahydronapthalene)-2,3,4,5-tetrahydro-1H-3-benzazepine hydrochloride, the product of Example 29, the title compound was prepared, m.p. 256°-257° C.; DCl MS M/Z:372 (M+H)+; IR (KBr):3440, 2950, 1600, 1480, 760 cm$^{-1}$; $^1$H NMR (CD$_3$OD) δ 1.60 (m, 1H), 1.85 (m, 1H), 2.08 (m, 1H), 2.33 (m, 1H), 2.87 (m, 2), 3.00 (s, 3H), 3.20–3.60 (m, 4H), 4.03 (m, 1H), 6.12 (s, 1H), 7.08 (m, 2H), 7.25 (m, 2H), 7.34 (s, 1H). Analysis calculated for $C_{20}H_{23}BrClNO \cdot 0.5HCl$: C, 56.26; H, 5.55; N, 3.28. Found: C, 55.88; H, 5.46; N, 3.24.

EXAMPLE 32

8-Hydroxy-7-methoxy-3-methyl-1-(spiro-5'-6',7',8',9'-tetrahydro-5'H-benzocycloheptene)-2,3,4,5-tetrahydro-1H-3-benzazepine hydrochloride Following the procedures described in Examples 1, 4, 5 and 10, replacing 1-indanone with benzosuberone (commercially available from Aldrich Chemical Company), the title compound was prepared, m.p. 242°–245° C.; DCl MS M/Z:338 (M+H)+; IR (KBr): 3420, 2940, 2680, 1610, 1590, 1500, 1460, 1280, 1240, 760 cm$^{-1}$; $^1$H NMR (CDCl$_3$) δ 1.50–1.82 (m, 6H), 2.18–2.29 (m, 1H), 2.38 (s, 3H), 2.44–2.60 (m, 2H), 2.67–2.77 (m, 1H), 2.83–3.02 (m, 3H), 3.15–3.30 (m, 1H), 3.86 (s, 3H), 6.29 (s, 1H), 6.57 (s, 1H), 7.04–7.11 (m, 3H), 7.13–7.20 (m, 1H). Analysis calculated for $C_{22}H_{28}ClNO_2$: C, 69.35; H, 7.80; N, 3.85. Found: C, 69.26; H, 7.53; N, 3.69.

EXAMPLE 33

8-Hydroxy-3-methyl-1-(spiro-5'-6',7',8',9'-tetrahydro-5'H-benzocycloheptene)-2,3,4,5-tetrahydro-1H-3-benzazepine hydrochloride Following the procedures described in Examples 1, 3, 12 and 14, replacing 1-indanone with benzosuberone (commercially available from Aldrich Chemical Company), the title compound was prepared, m.p. 225°–228° C.; DCl MS M/Z: 308 (M+H)+; IR (KBr): 3420, 3220, 2920, 2680, 1610, 1490, 1460, 1230, 820, 760 cm$^{-1}$; $^1$H NMR (CD$_3$OD) δ 1.60–2.10 (m, 5H), 2.20–2.53 (m, 2H), 2.82–2.98 (s, 2H), 2.92 (s, 1H), 2.99 (s, 2H), 3.05–3.18 (m, 1), 3.19–3.26 (m, 2H), 3.73 (d, ⅔H, J=15 Hz), 3.85 (d, ⅓H, J=15 Hz), 15 Hz), 4.25 (d, ⅓H, J=3.98 (d, ⅔H, J=15 Hz), 6.39 (d, ⅔H, J=3 Hz), 6.61–6.66 (m, 1H), 6.71 (dd, ⅓H, J=3, 8 Hz), 6.81–6.85 (m, ⅓H), 6.89–6.95 (m, ⅔H), 7.03–7.30 (m, 4H). Analysis calculated for $C_{21}H_{26}ClNO \cdot 0.1H_2O \cdot 0.5HCl$: C, 69.31; H, 7.40; N, 3.85. Found: C, 69.17; H, 7.41; N, 3.85.

EXAMPLE 34

7.8-Dihydroxy-3-methyl-1-(spiro-5'-6',7',8',9'-tetrahydro-5'H-benzocycloheptene)-2,3,4,5-tetrahydro-1H-3-benzazepine hydrobromide Following the procedures described in Examples 1, 6 and 16, replacing 1-indanone with benzosuberone (commercially available from Aldrich Chemical Company), the title compound was prepared, m.p. 324° C.; DCl MS M/Z: 338 (M+H)+; IR (KBr):3400, 2940, 1620, 1600, 1520, 1460, 1270, 760 cm$^{-1}$; $^1$H NMR (CD$_3$OD) δ 1.51–2.05(m, 5H), 2.16–2.50 (m, 2H), 2.76–2.95 (m, 1H), 2.91 (s, 1H), 2.98 (s, 2H), 3.05–3.17 (m, 2H), 3.20–3.40 (m, 1H), 3.60–3.70 (m, 1H), 3.74 (d, ⅔H, J=15 Hz), 3.80 (d, ⅓H, J=15 Hz), 3.91 (d, ⅔H, J=15 Hz), 4.22 (d, ⅓H, J=15 Hz), 6.40 (s, ⅔H), 6.60 (s, ⅓H), 6.63 (s, ⅔H), 6.67 (s, ⅓H), 6.84–6.92 (m, 1H), 7.07–7.25 (m, 3H). Analysis calculated for $C_{21}H_{26}BrNO_2 \cdot 0.2NH_4Br \cdot 0.1HBr$: C, 58.39; H, 6.28; N, 3.89 Found: C, 58.20; H, 6.24; N, 3.85.

EXAMPLE 35

7-Bromo-8-hydroxy-3-methyl-1-(spiro-5'-6',7',8',9'-tetrahydro-5'H-benzocycloheptene)-2,3,4,5-tetrahydro-1H-3-benzazepine hydrochloride Following the procedures described in Example 17, replacing 8-hydroxy-1-(spiro-1'-indan)-2,3,4,5-tetrahydro-1H-3-benzazepine hydrobromide with 8-hydroxy-3-methyl-1-(spiro-5'-6',7',8',9'-tetrahydro-5'H-benzocycloheptene)-2,3,4,5-tetrahydro-1H-3-benzazepine hydrochloride (the product of Example 33), the title compound was prepared, m.p. 250° C. (dec); IR (KBr): 3430, 3060, 2940, 2700, 1620, 1600, 1520, 1490, 1460, 1400, 1220, 760 cm$^{-1}$; $^1$H NMR (CD$_3$OD) δ 1.59–2.08 (m, 4H), 2.20–2.50 (m, 2H), 2.80–3.03 (m, 2H), 2.93 (s, 1H), 3.00 (s, 2H), 3.06–3.39 (m, 3H), 3.64–3.75 (m, 1⅔H, J=15 Hz)̣, 3.85 (d, ⅓H, J=15 Hz), 3.99 (d, ⅔H, J=15 Hz), 4.27 (d, ⅓H, J=15 Hz), 6.46 (s, ⅔H), 6.76 (s, ⅓H), 6.79–6.85 (m, ⅓H), 6.94–7.00 (m, ⅔H), 7.10–7.30 (m, 3H), 7.36 (s, 2/H), 7.42 (s, ⅓H). Analysis calculated for $C_{21}H_{25}BrClNO$: C, 59.66; H, 5.96; N, 3.31. Found: C, 59.52; H, 6.09; N, 3.22.

EXAMPLE 36

7-Carboxy-8-hydroxy-1-(spiro-1'-indan)-2,3,4,5-tetrahydro-1H-3-benzazepine hydrochloride Step 1:
7-Bromo-8-hydroxy-3-t-butyloxycarbonyl-1-(spiro-1'-indan)-2,3,4,5-tetrahydro-1H-3-benzazepine To a solution of 7-bromo-8-hydroxy-1-(spiro-1'-indan)-2,3,4,5-tetrahydro-1H-3-benzazepine (0.9 g, 2.6 mmol), the free base of the product of Example 17, in 30 mL of THF, was added a solution of di-t-butyl dicarbonate (0.7 g, 3.1 mmol) in 2 mL of THF. The reaction mixture was stirred overnight at ambient temperature and then the reaction was quenched by the addition of 4M aqueous ammonium hydroxide solution (300 mL). After stirring for 15 minutes, the quenched reaction mixture was extracted with diethyl ether (3×150 mL). The combined organic phase was washed with brine (200 mL), dried over anhydrous magnesium sulfate, filtered and concentrated in vacuo to give 1.0 g (87% yield) of the title compound. $^1$H NMR and mass spectral analysis were consistent with the assigned structure and the product was carried on to the next step without purification.

Step 2:
7-Bromo-8-methoxymethoxy-3-t-butyloxycarbonyl-1-(spiro-1'-indan)-2,3,4,5-tetrahydro-1H-3-benzazepine To a solution of the product of Step 1 (1.0 g, 2.3 mmol) in DMF (25 mL) at 0° C., was added sodium hydride (70 mg, 2.9 mmol). The reaction mixture was stirred at 0° C. for 35 minutes and then chloromethyl methyl ether (200 mg, 2.3 mmol) was added. After being stirred for 1.5 hour at ambient temperature, the reaction was quenched with methanol (10 mL). Water (400 mL) was added and the resultant mixture was extracted with diethyl ether (3×250 mL). The combined organic phase was washed with brine (300 mL), dried over anhydrous magnesium sulfate, filtered and concentrated in vacuo to give 1.28 g of the title compound as a pale yellow glass. The product was carried on without purification. The assigned structure was consistent with the mass spectral and $^1$H NMR analyses of the crude product, which was carried on without purification.

Step 3:
7-Carboxy-8-methoxymethoxy-3-t-butyloxycarbonyl-1-(spiro-1'-indan)-2,3,4,5-tetrahydro-1H-3-benzazepine To a solution of the product of Step 2 (1.11 g, 2.3 mmol) in 25 mL of THF under nitrogen atmosphere, at −78° C., was added 2.5M n-butyl lithium in hexane (1.0 mL, 2.5 mmol). The reaction mixture was stirred at −78° C. for 3 hours. Excess carbon dioxide, from dry ice, was passed over anhydrous calcium sulfate and bubbled into the reaction mixture at −78° C. The reaction mixture was left overnight to stir and to slowly come to ambient temperature. Diethyl ether (200 mL) was then added and the reaction mixture was washed successively with 0.5M aqueous ammonium chloride solution, water (2×200 mL) and brine (200 mL). The organic layer was dried over anhydrous magnesium sulfate, filtered and concentrated in vacuo to give a pale yelllow oil. The oil was chromatographed on silica gel eluting with acetic acid/ethyl acetate/hexane (1:30:70) to afford 0.33 g (32% yield) of the title compound; $^1$H NMR (CD$_3$OD) δ 1.38 (br s, 4H), 1.47 (br s, 5H), 2.1-2.14 (m, 1H), 2.48-2.59 (m, 1H), 2.8-3.33 (m, 5H), 3.36 (s, 3H), 3.46-3.66 (m, 1H), 3.95-4.25 (m, 2H), 5.06 (s, 2H), 6.56-6.65 (m, 1H), 6.92-7.06 (m, 1H), 7.17-7.36 (m, 3H), 7.95 (s, 1H).

Step 4:
7-Carboxy-8-hydroxy-1-(spiro-1'-indan)-2,3,4,5-tetrahydro-1H-3-benzazepine hydrochloride To a solution of the product of Step 3 (0.33 g, 0.73 mmol) in 30 mL of THF was added 4 mL of 5M hydrogen chloride in diethyl ether. The reaction mixture was allowed to stir at ambient temperature overnight and 6 mL of 2N aqueous hydrochloric acid was added. The reaction mixture was then heated at reflux for 5 hours. The reaction mixture was concentrated in vacuo and the residue was chased with THF and methylene chloride until a dry white powder was obtained. THF (2 mL) and diethyl ether (50 mL) were added to the powder and the suspension was stirred vigorously for 2 hours. The fine, white powder was filtered and dried in vacuo to afford 0.30 g (quantitative yield) of the title compound; DCl MS M/Z: 310 (M+H)$^+$; IR (KBr): 3420, 2950, 2840, 1670, 1615, 1415, 1190, 795, 755, 720, 695 cm$^{-1}$; $^1$H NMR (CD$_3$OD) δ 2.40-2.57 (m, 2H), 2.78-2.91 (m, 1H), 2.95-3.05 (m, 1H), 3.13-3.26 (m, 2H), 3.37-3.50 (m, 1H), 3.54 (d, 1H, J=14 Hz), 3.58-3.68 (m, 1H), 3.85 (d, 1H), 5.93 (s, 1H), 7.19-7.24 (m, 1H), 7.31-7.43 (m, 3H), 7.76 (s, 1H). Analysis calculated for C$_{19}$H$_{20}$ClNO$_3$: C, 65.99; H, 5.83; N, 4.05. Found: C, 65.56; H, 5.97; N, 3.89.

EXAMPLES 37-85

Following the procedures described in Examples 1 and 2, the indane intermediates for the synthesis of Examples 37-85 are prepared from the appropriate readily available indanone starting materials. The condensation of these intermediates with the appropriate phenyl acetyl chlorides (the compounds of Examples 3 and 4) to afford the cyclic lactam intermediates is carried out using the procedures described in Examples 5, 6 and 12. The compounds of Examples 37-85, disclosed in Table 4, are prepared from these intermediates using the procedures described in Examples 9, 10, 11, 13, 14, 15, 16, 17, 18, 19, 20, 21, 22, and 23.

TABLE 4
Examples 37-85

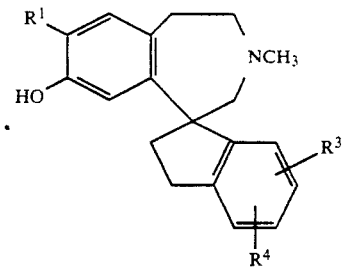

| Example No. | R$^1$ | R$^3$ | R$^4$ |
|---|---|---|---|
| 37 | OMe | H | CH$_3$ |
| 38 | H | H | CH$_3$ |
| 39 | OH | H | CH$_3$ |
| 40 | Br | H | CH$_3$ |
| 41 | NO$_2$ | H | CH$_3$ |
| 42 | NH$_2$ | H | CH$_3$ |
| 43 | NHC(O)CH$_3$ | H | CH$_3$ |
| 44 | OMe | H | Cl |
| 45 | H | H | Cl |
| 46 | OH | H | Cl |
| 47 | Br | H | Cl |
| 48 | NO$_2$ | H | Cl |
| 49 | NH$_2$ | H | Cl |
| 50 | NHC(O)CH$_3$ | H | Cl |
| 51 | OMe | H | F |
| 52 | H | H | F |
| 53 | OH | H | F |
| 54 | Br | H | F |
| 55 | NO$_2$ | H | F |
| 56 | NH$_2$ | H | F |
| 57 | NHC(O)CH$_3$ | H | F |
| 58 | OMe | H | OMe |
| 59 | H | H | OMe |
| 60 | OH | H | OMe |
| 61 | Br | H | OMe |
| 62 | NO$_2$ | H | OMe |
| 63 | NH$_2$ | H | OMe |
| 64 | NHC(O)CH$_3$ | H | OMe |
| 65 | OMe | H | OH |
| 66 | H | H | OH |
| 67 | OH | H | OH |
| 68 | Br | H | OH |
| 69 | NO$_2$ | H | OH |
| 70 | NH$_2$ | H | OH |
| 71 | NHC(O)CH$_3$ | H | OH |
| 72 | OMe | OMe | OMe |
| 73 | H | OMe | OMe |
| 74 | OH | OMe | OMe |
| 75 | Br | OMe | OMe |
| 76 | NO$_2$ | OMe | OMe |
| 77 | NH$_2$ | OMe | OMe |
| 78 | NHC(O)CH$_3$ | OMe | OMe |
| 79 | OMe | OH | OH |
| 80 | H | OH | OH |
| 81 | OH | OH | OH |
| 82 | Br | OH | OH |
| 83 | NO$_2$ | OH | OH |
| 84 | NH$_2$ | OH | OH |
| 85 | NHC(O)CH$_3$ | OH | OH |

EXAMPLES 86-134

Following the procedures described in Examples 7 and 8, the amino intermediates for the synthesis of Examples 86-134 are prepared from the appropriate readily available α-tetralone starting materials. The condensation of these intermediates with the appropriate phenyl acetyl chlorides (the compounds of Examples 3 and 4) to afford the cyclic lactam intermediates is carried out using the procedures described in Examples 5, 6 and 12. The compounds of Examples 86-134, disclosed in Table 5, are prepared from these intermediates using the procedures described in Examples 9, 10, 11, 13, 14, 15, 16, 17, 18, 19, 20, 21, 22, and 23.

TABLE 5

Examples 86-134

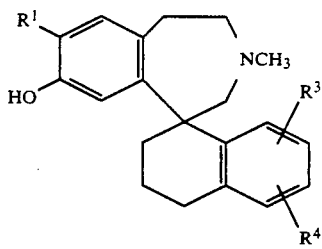

| Example No. | R¹ | R³ | R⁴ |
|---|---|---|---|
| 86 | OMe | H | CH₃ |
| 87 | H | H | CH₃ |
| 88 | OH | H | CH₃ |
| 89 | Br | H | CH₃ |
| 90 | NO₂ | H | CH₃ |
| 91 | NH₂ | H | CH₃ |
| 92 | NHC(O)CH₃ | H | CH₃ |
| 93 | OMe | H | Cl |
| 94 | H | H | Cl |
| 95 | OH | H | Cl |
| 96 | Br | H | Cl |
| 97 | NO₂ | H | Cl |
| 98 | NH₂ | H | Cl |
| 99 | NHC(O)CH₃ | H | Cl |
| 100 | OMe | H | F |
| 101 | H | H | F |
| 102 | OH | H | F |
| 103 | Br | H | F |
| 104 | NO₂ | H | F |
| 105 | NH₂ | H | F |
| 106 | NHC(O)CH₃ | H | F |
| 107 | OMe | H | OMe |
| 108 | H | H | OMe |
| 109 | OH | H | OMe |
| 110 | Br | H | OMe |
| 111 | NO₂ | H | OMe |
| 112 | NH₂ | H | OMe |
| 113 | NHC(O)CH₃ | H | OMe |
| 114 | OMe | H | OH |
| 115 | H | H | OH |
| 116 | OH | H | OH |
| 117 | Br | H | OH |
| 118 | NO₂ | H | OH |
| 119 | NH₂ | H | OH |
| 120 | NHC(O)CH₃ | H | OH |
| 121 | OMe | OMe | OMe |
| 122 | H | OMe | OMe |
| 123 | OH | OMe | OMe |
| 124 | Br | OMe | OMe |
| 125 | NO₂ | OMe | OMe |
| 126 | NH₂ | OMe | OMe |
| 127 | NHC(O)CH₃ | OMe | OMe |
| 128 | OMe | OH | OH |
| 129 | H | OH | OH |
| 130 | OH | OH | OH |
| 131 | Br | OH | OH |
| 132 | NO₂ | OH | OH |
| 133 | NH₂ | OH | OH |
| 134 | NHC(O)CH₃ | OH | OH |

EXAMPLE 135

8-Hydroxy-7-methoxy-3-methyl-1-(spiro-4'-(3',4'-dihydro-2'H-1'-benzopyran))-2,3,4,5-tetrahydro-1H-3-benzazepine hydrochloride Step 1:
N-(4-benzyloxy-3-methoxyphenylacetyl)-4-aminomethyl-2H-1-benzopyran 4-Benzyloxy-3-methoxyphenylacetyl chloride, prepared as described in Example 4, and 4-aminomethyl-2H-1-benzopyran, prepared as described in Step 1 of Example 136, were condensed as described in Step 1 of Example 6 to give the lactam, N-(4-benzyloxy-3-methoxyphenylacetyl)-4-aminomethyl-2H-1-benzopyran.

Step 2

The product of Step 1 (1.8 g, 5.5 mmol) was added to 100 mL of methane sulfonic acid and the reaction mixture was stirred at ambient temperature for 16 hours. The reaction mixture was then poured over ice (~400 mL) and the aqueous mixture was extracted with methylene chloride (3×200 mL). The combined organic phase was dried over anhydrous magnesium sulfate, filtered and concentrated in vacuo to give a tan foam. The foam was chromatographed on silica gel eluting with ethyl acetate/methylene chloride (1:1) to afford 0.68 g (38% yield) of the title compound; $^1$H NMR (CD$_3$OD) δ 1.84-1.94 (m, 1H), 1.95-2.05 (m, 1H), 3.42 (s, 2H), 3.48 (d, 1H, J=13 Hz), 3.68 (d, 1H, J=13 Hz), 3.83 (s, 3H), 4.14-4.21 (m, 2H), 6.64-6.76 (m, 3H), 6.81-6.88 (m, 2H), 7.08-7.16 (m, 1H), 7.39 (dd, 1H, J=2 Hz, 9 Hz).

Step 3:
4-(N-(2-(4-hydroxy-3-methoxyphenyl)ethyl)-N-methylamino)-4-hydroxy-2H-1-3,4-dihydrobenzopyran To a solution of the product of Step 2 (340 mg, 1.05 mmol) in 20 mL of THF at 0° C., was added 3.2 mL (3.2 mmol) of a 1M solution of borane-THF complex in THF. The reaction mixture was allowed to warm to ambient temperature and was stirred for 7 hours. Aqueous 2N hydrochloric acid solution (20 mL) was then added slowly and stirring was continued for 15 minutes. The reaction mixture was made basic by the addition of concentrated ammonium hydroxide and then extracted with methylene chloride (2×100 mL). The combined organic phase was dried over anhydrous magnesium sulfate, filtered and concentrated in vacuo to give a yellow glass. This material was taken up in acetonitrile (20 mL) and 37% aqueous formaldehyde (0.34 mL, 4.2 mmol) was added, followed by sodium cyanoborohydride (190 mg, 3.15 mmol). The reaction mixture was stirred at ambient temperature for 5 hours and then 2N aqueous hydrochloric acid was added. Stirring was continued for 15 minutes. The reaction mixture was made basic by the addition of concentrated ammonium hydroxide and extracted with methylene chloride (3×100 mL). The combined organic phase was washed with brine (2×200 mL), dried over anhydrous magnesium sulfate, filtered and concentrated under reduced pressure to give a clear oil. The oil was chromatographed on silica gel eluting with ethyl acetate/methylene chloride/ammonium hydroxide (50:50:1) to afford 185 mg (51% yield) of the title compound; $^1$H NMR (CDCl$_3$) δ 2.00-2.07 (m, 2H), 2.47 (s, 3H), 2.66-2.84 (m, 5H), 2.89 (d, 1H, J=13 Hz), 3.89 (s, 3H), 4.12-4.29 (m, 2H), 5.5 (br s, 1H), 6.66–6.71 (m, 2H), 6.76–6.94 (m, 3H), 7.11–7.19 (m, 1H), 7.49 (dd, 1H, J=3 Hz, 8 Hz).

Step 4:
8-Hydroxy-7-methoxy-3-methyl-1-(spiro-4′-(3′,4′-dihydro-2′H-1′-benzopyran))-2,3,4,5-tetrahydro-1H-3-benzazepine hydrochloride Methane sulfonic acid (~10–12 mL) was added to the product of Step 3 (180 mg, 0.52 mmol) and the reaction mixture was stirred at ambient temperature for 24 hours. The reaction mixture was diluted with methylene chloride (200 mL) and made basic by the addition of aqueous 5M ammonium hydroxide (~250 mL). The aqueous layer was extracted with methylene chloride (200 mL) and the combined organic phase was dried over anhydrous magnesium sulfate, filtered and concentrated in vacuo to give a white foam. This material was chromatographed on silica gel eluting with ethyl acetate/methylene chloride/ammonium hydroxide (50:50:1) to afford 87 mg of the free base of the title compound. The free base was dissolved in isopropanol (~0.3 mL) and diethyl ether (~2.5 mL). A solution of hydrogen chloride in diethyl ether (0.5 mL) was added and the resultant precipitate collected by filtration to give 75 mg (40% yield) of the title compound; DCI MS M/Z: 326 (M+H)$^+$; IR (KBr): 3420, 2940, 2700, 1580, 1515, 1280, 1220, 760 cm$^{-1}$; $^1$H NMR (CD$_3$OD) δ 2.24–2.47 (m, 2H), 3.03 (s, 3H), 3.12–3.23 (m, 1H), 3.25–3.42 (m, 2H), 3.57–3.66 (m, 1H), 3.70–3.80 (m, 2H), 3.83 (s, 3H), 4.04 (d, 1H, J=14 Hz), 4.21 (dt, 1H, J=3 Hz, 12 Hz), 6.15 (s, 1H), 6.82 (s, 1H), 6.9–7.01 (m, 2H), 7.11 (dd, 1H, J=2 Hz, 7 Hz), 7.21–7.29 (m, 1H). Analysis calculated for C$_{20}$H$_{24}$ClNO$_3$. 0.2C$_3$H$_7$OH.0.6HCl: C, 62.52; H, 6.67; N, 3.54. Found: C, 62.31; H, 6.69; N, 3.57.

EXAMPLE 136

8-Hydroxy-3-methyl-1-(spiro-4′-(3′,4′-dihydro-2′-H-1′-benzopyran))-2,3,4,5-tetrahydro-1H-3-benzazepine hydrochloride Step 1:
4-Aminomethyl-4-hydroxy-2H-1-3,4-dihydrobenzopyran To a stirred solution of 4-chromanone (10 g, 68 mmol), commercially available from Aldrich Chemical Company, in 200 mL of anhydrous THF, was added 0.5M lithium cyanide in DMF (4 mL, 2 mmol) at ambient temperature. To this turbid solution was then added trimethylsilyl cyanide (18 mL, 140 mmol) in one portion. The resultant solution was allowed to stir at ambient temperature for 5 hours and then solvents were removed under reduced pressure to give an oil. The oil was dissolved in 100 mL of anhydrous THF and the resultant solution was added, over a period of 10 minutes, to a refluxing suspension of lithium aluminum hydride (2.6 g, 200 mmol) in 200 mL of THF. The reaction mixture was heated at reflux for 2 hours and then allowed to cool to ambient temperature, diluted with 500 mL of THF and quenched with excess sodium sulfate decahydrate. The solid was removed by filtration through Celite ® and the filtrate was concentrated in vacuo to give 15 g of the title compound as a light brown oil; $^1$H NMR (CDCl$_3$) δ 2.07 (tt 2H, J=1.5 Hz, 7.0 Hz), 2.96 (d, 2H, J=13 Hz), 3.08 (d, 1H, J=13 Hz), 4.25 (m, 2H), 6.83 (dd, 1H, J=1.5 Hz, 9 Hz), 6.95 (m, 1H), 7.19 (m, 1H), 7.43 (dd, 1H, J=1.7 Hz, 8.2 Hz).

Step 2:
N-(4-Methoxy-3-methylthiophenylacetyl)-4-aminomethyl-4-hydroxy-2H-1-3,4-dihydrobenzopyran To a stirred solution of (4-methoxy-3-methylthio)-phenylacetic acid (12.63 g, 60 mmol) in 250 mL of anhydrous THF, at ambient temperature, was added, via syringe, oxalyl chloride (6 mL, 70 mmol). To the resulting solution was added 5 drops of DMF and the reaction mixture was allowed to stir at ambient temperature for 2 hours. The solvents were removed under reduced pressure and the residue was dissolved in methylene chloride (150 mL). The resultant solution was added to a vigorously stirred mixture of saturated sodium bicarbonate (400 mL) and methylene chloride (250 mL) containing the product of Step 2 (10.66 g, 60 mmol). The reaction mixture was stirred for 1.5 hour and then it was diluted with water and the layers were separated. The aqueous layer was washed with methylene chloride (2×100 mL). The combined organic phase was dried over anhydrous magnesium sulfate, filtered and concentrated under reduced pressure to give 20 g of the tilte compound as a tan solid; $^1$H NMR (CDCl$_3$) δ 1.95 (m, 2H), 2.42 (s, 3H), 3.55 (s, 2H), (s, 2H), 3.87 (s, 3H), 4.21 (t, 2H, J=6.0 Hz), 5.82 (t, 1H, J=4.5 Hz), 6.8 (m, 2H), 6.88 (m, 1H), 6.97 (m, 1H), 7.16 (m, 1H), 7.32 (dd, 1H, J=2 Hz, 6.0 Hz).

Step 3:
4-(N-(2-(4-Methoxy-3-methylthiophenyl)ethyl-N-methyl)aminomethyl-4-hydroxy-3,4-dihydro-2′H-1′-benzopyran To a stirred solution of the product of Step 2(9.15 g, 24.5 mmol) in 240 mL of anhydrous THF, at −10° C., was added in one portion, 75 mL of a 1M solution of borane-THF complex in THF (75 mmol). After the addition was complete the cooling bath was removed and the resultant solution was allowed to stir for 4.5 hours. The reaction was quenched by the addition of 30% aqueous ammonium hydroxide (400 mL) and the resultant aqueous mixture was extracted with diethyl ether (3×200 mL). The combined organic phase was dried over anhydrous magnesium sulfate, filtered and concentrated under reduced pressure. The residue was dissolved in actonitrile (240 mL) and formalin (7.5 mL of 37% aqueous formaldehyde, 98 mmol) was added, followed by sodium cyanoborohydride (6.2 g, 98 mmol). The reaction mixture was stirred for 8 hours and then the reaction was quenched with 30% aqueous ammonium hydroxide (400 mL). The resultant aqueous mixture was extracted with diethyl ether (3×300 mL) and the combined organic phase dried over anhydrous magnesium sulfate, filtered and concentrated under reduced pressure. The residue was purified by chromatography on silica gel eluting with ethyl acetate/methylene chloride/ammonium hydroxide (95:4:1) to give 4.7 g of the title compound as a colorless oil; $^1$H NMR (CDCl$_3$) δ 2.05 (m, 2H), 2.43 (s, 3H), 2.5 (br s, 3H), 2.7–2.95 (m, 6H), 3.85 (m, 2H), 3.90 (s, 3H), 4.20 (m, 2H), 6.78 (m, 2H), 6.97 (m, 3H), 7.15 (m, 1H), 7.40 (m, 1H).

Step 4:
8-Methoxy-3-methyl-7-methylthio-1-(spiro-4′-(3′,4′-dihydro-2′H-1′-benzopyran))-2,3,4,5-tetrahydro-1H-3-benzazepine To a solution of the product of Step 3 (4.7 g, 13 mmol) in 130 mL of methylene chloride was added 25 mL of methanesulfonic acid. The resultant solution was stirred at ambient temperature for 2 hours and then poured over ice and diluted with methylene chloride (400 mL). Ammonium hydroxide was added until the aqueous layer was basic and then the layers were separated. The aqueous layer was extracted with methylene chloride (2×300 mL) and the combined organic phase was washed with water (2×400 mL), dried over anhydrous magnesium sulfate, filtered and concentrated in vacuo to a yellow oil. The oil was dissolved in 250 mL of diethyl ether/THF (1:1) and extracted with 2N aquoeus hydrochloric acid solution (3×200 mL). The combined acidic aqueous extracts were washed with diethyl ether and made basic by the addition of 3M aqueous sodium hydroxide solution. The basic solution was extracted with methylene chloride (3×200 mL) and the combined methylene chloride extract was washed with water, dried over anhydrous magnesium sulfate, filtered and concentrated under reduced pressure to give 2.52 g of the title compound as a light yellow glass; $^1$H NMR (CDCl$_3$) δ 2.35 (m, 2H), 2.40 (s, 6H), 2.7–3.0 (m, 4H), 3.3 (m, 1H), 3.48 (s, 3H), 3.85 (m, 2H), 4.12 (m, 1H), 6.13 (s, 1H), 6.88 (m, 2H), 6.91 (s, 1H), 7.15 (m, 1H).

Step 5:
8-Methoxy-3-methyl-1-(spiro-4'-(3',4'-dihydro-2'H-1'-benzopyran))-2,3,4,5-tetrahydro-1H-3-benzazepine To a solution of the product of Step 4 (2.52 g, 7.1 mmol) in 250 mL of absolute ethanol was added 25 g of Raney Nickel. The resulting mixture was heated at reflux until uptake of hydrogen gas ceased. The reaction mixture was then filtered through Celite ® and the filtrate was concentrated in vacuo to give 2.1 g of the title compound as a tan solid; $^1$H NMR (CDCl$_3$) δ 2.30 (m, 2H), 2.39 (s, 3H), 2.45 (m, 1H), 2.7–3.05 (m, 4H), 3.30 (m, 1H), 3.6 (s, 3H), 3.8 (m, 1H), 4.10 (m, 1H), 6.23 (d, 1H, J=3 Hz), 6.62 (dd, 1H, J=3 Hz, 9 Hz), 6.87 (m, 2H), 7.03 (m, 1H), 7.16 (m, 2H).

Step 6:
8-Hydroxy-3-methyl-1-(spiro-4'-(2'H-1'-3',4'-dihydrobenzopyran))-2,3,4,5-tetrahydro-1H-3-benzazepine hydrochloride To a solution of the product of Step 5 (2.1 g, 6.7 mmol) in 70 mL of anhydrous methylene chloride, cooled to −78 C., was added 13.4 mL of a 1M solution of boron tribromide in methylene chloride (13.4 mmol). The cooling bath was then removed and the reaction mixture was allowed to warm to ambient temperature. The reaction mixture was stirred for 2 hours and then cooled to −78° C. The reaction was quenched by the addition of anhydrous methanol and then allowed to warm to ambient temperature. Solvent was evaporated under reduced pressure and the residue was chased with methanol (2×100 mL). The residue was then chromatographed on silica gel eluting with ethyl acetate/methylene chloride/ammonium hydroxide (95:5:1) to give 1.38 g of the product as the free base, which was dissolved in methanol/diethyl ether. A saturated solution of hydrogen chloride in diethyl ether was added and the resultant precipitate was filtered and dried in vacuo to give the title compound as a fine white powder, m.p. 255 (dec); IR (KBr): 3450, 2700, 1600, 1480, 1220 cm$^{-1}$; $^1$H NMR (CD$_3$OD) δ 2.28 (m, 2H), 2.32 (s, 3H), 2.43 (m, 1H), 2.8 (m, 2H), 2.95 (m, 2H), 3.28 (m, 1H), 3.80 (m, 1H), 4.1 (m, 1H), 6.1 (d, 1H, J=3 Hz), 6.57 (dd, 1H, J=3 Hz, 9 Hz), 6.85 (m, 2H), 6.97 (d, 2H, J=9 Hz), 7.12 (m, 2H). Analysis calculated for C$_{19}$H$_{22}$ClNO$_2$: C, 68.77; H, 6.68; N, 4.22. Found: C, 68.56; H, 6.60; N, 4.17.

EXAMPLE 137

7-Bromo-8-hydroxy-3-methyl-1-(spiro-4'-(3',4'-dihydro-2'H-1'-benzopyran))-2,3,4,5-tetrahydro-1H-3-benzazepine hydrochloride Bromine (0.75 g, 4.7 mmol) was added to a solution of 8-hydroxy-3-methyl-1-(spiro-4'-(3',4'-dihydro-2'H-1'-benzopyran))-2,3,4,5-tetrahydro-1H-3-benzazepine hydrochloride (1.38 g, 4.7 mmol), prepared as described in Example 136, in 56 mL of formic acid/THF (8:1) at ~0° C. and the reaction mixture was allowed to stir overnight and slowly warm to ambient temperature. The reaction mixture was then poured over ice (~200 mL) and methylene chloride (400 mL) was added. Concentrated ammonium hydroxide was added until the aqueous layer became basic and the layers were separated. The organic layer was washed successively with water (3×300 mL) and brine (300 mL), dried over anhydrous magnesium sulfate, filtered and concentrated in vacuo to give a light brown oil. The oil was purified by flash chromatography on silica gel eluting with THF/methylene chloride (3:97) to afford 318 g of the desired product as the free base. The free base was taken up in ~5 mL of methylene chloride/THF and a saturated solution of hydrogen chloride in diethyl ether was added. The resultant precipitate was collected by filtration and dried in vacuo to afford 0.25 g (13% yield) of the title compound, m.p. 255 (dec); DCl MS M/Z: 374 (M+H)$^+$; 376 (M+2+H)$^+$; IR (KBr): 3430, 3070, 2950, 2650, 1600, 1580, 1485, 1400, 1220, 770, 755 cm$^{-1}$; $^1$H NMR (CD$_3$OD) δ 2.30–2.49 (m, 2H), 3.03 (s, 3H), 3.1–3.2 (m, 1H), 3.37–3.52 (m, 2H), 3.62 (d, 1H, J=13 Hz), 3.68–3.85 (m, 2H), 4.07 (d, 1H, J=13 Hz), 4.18–4.28 (m, 1H), 6.30 (s, 1H), 6.91–7.04 (m, 2H), 7.1–7.17 (m, 1H), 7.22–7.30 (m, 1H), 7.38 (s, 1H). Analysis calculated for C$_{19}$H$_{21}$BrClNO$_2$: C, 55.56; H, 5.15; N, 3.41. Found: C, 55.50; H, 5.24; N, 3.31.

EXAMPLE 138

7-Bromo-8-hydroxy-3-methyl-1-(spiro-4'-(2'H-1'-3',4'-dihydrobenzopyran))-2,3,4,5-tetrahydro-1H-3-benzazepine hydrochloride Bromine (15 mg, 0.95 mmol) was added to a solution of 8-hydroxy-3-methyl-1-(spiro-4'-(3',4'-dihydro-2'H-1'-benzopyran))-2,3,4,5-tetrahydro-1H-3-benzazepine hydrochloride (62 mg, 0.19 mmol), prepared as described in Example 136, in 4 mL of formic acid/THF (3:1) at ~−10° C. and the reaction mixture was stirred for 7 minutes. Cooling was discontinued and the reaction mixture was allowed to slowly warm to ambient temperature. The reaction mixtuire was stirred for 5.5 hours, cooled to −10° C. and additional bromine (15 mg, 0.95 mmol) was added. The reaction mixture was again allowed to slowly warm to ambient temperature and was stirred overnight. The reaction mixture was then poured over ice (~200 ml) and methylene chloride (200 mL) was added. Concentrated ammonium hydroxide was added until the aqueous layer was basic and then the layers were separated. The aqueous layer was extracted with methylene chloride (200 mL) and the combined organic phase was dried over anhydrous magnesium sulfate, filtered and concentrated in vacuo to give 130 mg of a white solid. This material was chromatographed on silica gel eluting with methylene chloride saturated with ammonium hydroxide to afford the desired product as the free base. The free base was taken up in ~5 mL of methanol amd methylene chloride (~3 mL) and diethyl ether saturated with hydrogen chloride was added. The crystals which formed were collected by filtration and dried in vacuo to afford 45 mg (48% yield) of the title compound, m.p. 255 (dec); High Resolution Mass Spectrum: mass calculated for $C_{19}H_{19}Br_2NO_2$: 450.9784; exact mass measured: 450.9786; IR (KBr): 3430, 3140, 2960, 2710, 2290, 1480, 1465, 1400, 1220, 1050, 930, 830 cm$^{-1}$; $^1$H NMR (CD$_3$OD) δ 2.26–2.46 (m, 2H), 3.04 (s, 3H), 3.10–3.21 (m, 1H), 3.23–3.47 (m, 2H), 3.64 (dd, 1H, J=2 Hz, 13 Hz), 3.68–3.81 (m, 2H), 4.11 (d, 1H, J=13 Hz), 4.25 (dt, 1H, J=11 Hz), 6.27 (s, 1H), 6.81 (d, 1H, J=9 Hz), 7.32 (d, 1H, J=3 Hz), 7.38–7.44 (m, 2H).

EXAMPLES 139–150

Following the procedures described in Examples 135 and 136, the benzopyran intermediates for the synthesis of Examples 139–150 are prepared from the appropriate readily-available benzopyranone starting materials. The condensation of these intermediates with the appropriate phenyl acetyl chlorides (the compounds of Examples 3 and 4) to afford lactams is carried out as described in Step 2 of Example 136. The compounds of Examples 139 and 150, disclosed in Table 6, are prepared from these lactam intermediates according to the procedures described in Steps 2–4 of Example 135 and Example 16 ($R^1$=OH), Example 21 ($R^1$=NO$_2$) and Example 22 ($R^1$=NH$_2$). The compound wherein $R^1$ is carboxy is prepared as described in Example 36, substituting the indanone intermediate with the appropriate benzopyranone intermediate. The carboxy-compound ($R^1$=COOH) may then be converted by standard procedures (see, for example J. March, *Advanced Organic Chemistry: Reactions, Mechanisms and Structure*, Wiley-Interscience, 1985) into the compounds of Examples 143 (esterification), 144 (alkylation), 145 (alkylation), 146 (reduction), 147 (reduction/alkylation), 148 (reduction), 149 (conversion to amide) and 150 (conversion to amide/reduction).

TABLE 6

Examples 139–150

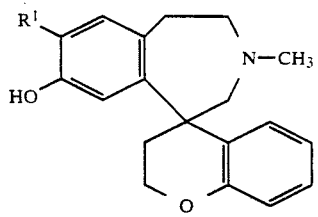

| Example No. | $R^1$ |
|---|---|
| 139 | SMe |
| 140 | OH |
| 141 | NO$_2$ |
| 142 | NH$_2$.HCl |
| 143 | CO$_2$CH$_3$ |
| 144 | C(O)CH$_3$ |
| 145 | CH(OH)CH$_3$ |
| 146 | CH$_2$OH |
| 147 | CH$_2$OCH$_3$ |
| 148 | CH$_3$ |
| 149 | C(O)NHCH$_3$ |
| 150 | CH$_2$NHCH$_3$ |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound having the formula:

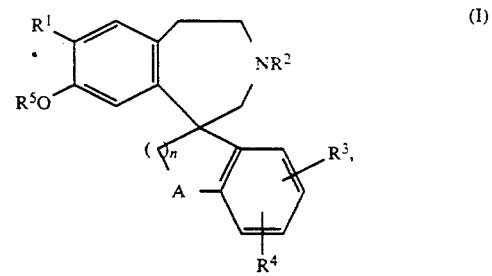

wherein
n is an integer of from 1-to-3;
A is CH$_2$, O or S;
$R^1$ is selected from the group consisting of
(1) hydrogen,
(2) C$_1$–C$_6$-alkyl,
(3) halogen,
(4) halo-C$_1$–C$_6$-alkyl,
(5) hydroxy,
(6) hydroxy-C$_1$–C$_4$-alkyl,
(7) C$_1$–C$_6$-alkoxy,
(8) C$_1$–C$_4$-alkoxymethyl,
(9) C$_1$–C$_6$-alkylthio,
(10) C$_1$–C$_6$-alkoxycarbonyl,
(11) C$_1$–C$_6$-alkylcarbonyl,
(12) C$_1$–C$_6$-alkylaminocarbonyl,
(13) nitro,
(14) amino,
(15) C$_1$–C$_6$-alkylamino,
(16) alkanoylamino,
(17) aminocarbonyl, and
(18) aminomethyl;
$R^2$ is selected from the group consisting of
(1) hydrogen,
(2) C$_1$–C$_6$-alkyl,
(3) alkanoyl,
(4) α-amino acid and
(5) dipeptide;
$R^3$ and $R^4$ are independently selected from the group consisting of
(1) hydrogen,
(2) C$_1$–C$_4$-alkyl,
(3) halogen,
(4) halo-C$_1$–C$_4$-alkyl,
(5) hydroxy,
(6) C$_1$–C$_4$-alkoxy,
(7) C$_1$–C$_4$-alkylthio,
(8) nitro,
(9) amino and
(10) C$_1$–C$_4$-alkylamino; and
$R^5$ is selected from the group consisting of
(1) hydrogen,
(2) alkanoyl, and
(3) alkylaminocarbonyl,
or a pharmaceutically-acceptable salt thereof.

2. A compound of claim 1 wherein A is —CH$_2$—.
3. A compound of claim 1 wherein A is oxygen.
4. A compound of claim 1 wherein A is sulfur.
5. A compound of claim 1 wherein $R^2$ is methyl.

6. A compound selected from the group consisting of:

8-Hydroxy-7-methoxy-1-(spiro-1'-1',2',3',4'-tetrahydronaphthalene)-2,3,4,5-tetrahydro-1H-3-benzazepine;

8-Hydroxy-3-methyl-7-methylthio-1 (spiro-1'-indan)-2,3,4,5-tetrahydro-1H-3-benzazepine;

8-Hydroxy-7-methylthio-1-(spiro-1'-indan)-2,3,4,5-tetrahydro-1H-3-benzazepine;

8-Hydroxy-3-methyl-1-(spiro-1'-indan)-2,3,4,5-tetrahydro-1H-3-benzazepine;

7-Bromo-8-hydroxy-1-(spiro-1'-indan)-2,3,4,5-tetrahydro-1H-3-benzazepine;

8-Hydroxy-3-methyl-7-nitro-1-(spiro-1'-indan)-2,3,4,5-tetrahydro-1H-3-benzazepine;

8-Hydroxy-7-methoxy-1-(spiro-1'-indan)-2,3,4,5-tetrahydro-1H-3-benzazepine;

7,8-Dihydroxy-3-methyl-1-(spiro-1'-1',2',3',4'-dihydronaphthalene)-2,3,4,5-tetrahydro-1H-3-benzazepine, 7-Bromo-8-hydroxy-1-(spiro-1'-1',2',3',4'-tetrahydronapthalene)-2,3,4,5-tetrahydro-1H-3-benzazepine;

8-Hydroxy-3-methyl-7-nitro-1-(spiro-1'-1',2',3',4'-tetrahydronapthalene)-2,3,4,5-tetrahydro-1H-3-benzazepine;

8-Hydroxy-7-methoxy-3-methyl-1-(spiro-4'-(3',4'-dihydro-2'H-1'-benzopyran))-2,3,4,5-tetrahydro-1H-3-benzazepine; and 8-Hydroxy-7-methoxy-3-methyl-1-(spiro-5'-(6',7',8',9'-tetrahydro-5'H-benzocycloheptene))-2,3,4,5-tetrahydro-1H-3-benzazepine, or a pharmaceutically-acceptable salt thereof.

7. A compound selected from the group consisting of:

8-Hydroxy-7-methoxy-3-methyl-1-(spiro-1'-1',2',3',4'-tetrahydro-naphthalene)-2,3,4,5-tetrahydro-1H-3-benzazepine;

8-Hydroxy-3-methyl-7-methylthio-1-(spiro-1'-1',2',3',4'-tetrahydronapthalene)-2,3,4,5-tetrahydro-1H-3-benzazepine;

7,8-Dihydroxy-3-methyl-1-(spiro-1'-indan)-2,3,4,5-tetrahydro-1H-3-benzazepine;

7-Bromo-8-hydroxy-3-methyl-1-(spiro-1'-indan)-2,3,4,5-tetrahydro-1H-3-benzazepine;

8-Hydroxy-7-methoxy-3-methyl-1-(spiro-1'-indan)-2,3,4,5-tetrahydro-1H-3-benzazepine; and 7-Bromo-8-hydroxy-3-methyl-1-(spiro-1'-1',2',3',4'-tetrahydronapthalene)-2,3,4,5-tetrahydro-1H-3-benzazepine, or a pharmaceutically-acceptable salt thereof.

8. A pharmaceutical composition for blocking dopamine receptors comprising a pharmaceutically-acceptable auxillary and a therapeutically-effective amount of a compound of claim 1.

9. A method for blocking dopaminergic receptors comprising administering to a human or other mammal in need a therapeutically-effective amount of a compound of claim 1.

10. A method for treating dopamine-related neurological disorders comprising administering to a human or other mammal in need a therapeutically-effective amount of a compound of claim 1.

11. A method for treating dopamine-related psychological disorders comprising administering to a human or other mammal in need a therapeutically-effective amount of a compound of claim 1.

12. A method for treating dopamine-related behavioral disorders comprising administering to a human or other mammal in need a therapeutically-effective amount of a compound of claim 1.

* * * * *